(12) United States Patent
Johnson et al.

(10) Patent No.: US 6,329,196 B1
(45) Date of Patent: Dec. 11, 2001

(54) METHODS AND APPARATUS FOR ENHANCEMENT OF MASS TRANSFER OF A FLUID IN A POROUS MATRIX SYSTEM CONTAINING BIOMASS

(76) Inventors: William Nevil Heaton Johnson, Cliffe House, Village du Petron, St. Peter Port (GB), GY1 4HP; Martin Davies, 3 Chumet View Road, Oakamoor Road, Stoke-on-Trent (GB), ST10 3AE; Charles Joseph Banks, 8 Old Priory Close, Hamble, Southampton (GB)

(*) Notice: Subject to any disclaimer, the term of this patent is extended or adjusted under 35 U.S.C. 154(b) by 0 days.

(21) Appl. No.: 09/320,529

(22) Filed: May 26, 1999

Related U.S. Application Data

(63) Continuation of application No. PCT/GB97/03179, filed on Nov. 19, 1997.

(30) Foreign Application Priority Data

Nov. 27, 1996 (GB) .................................................. 9624644
Sep. 10, 1997 (GB) .................................................. 9719278

(51) Int. Cl.$^7$ ................................................ C12M 1/10
(52) U.S. Cl. ................................ 435/299.1; 435/298.2; 435/180; 210/619; 210/150
(58) Field of Search ..................... 435/174, 180, 435/395, 399, 262, 262.5, 281, 282, 289.1, 289.2, 299.1, 243; 210/615–619, 150, 151

(56) References Cited

U.S. PATENT DOCUMENTS 3,027,305 * 3/1962 Freeman .
4,810,385 * 3/1989 Hater et al. .
5,256,298 * 10/1993 Powell .
5,531,897 * 7/1996 Stromo .
5,554,537 * 9/1996 Sharpe .

FOREIGN PATENT DOCUMENTS 35 30 332 * 5/1986 (DE) .
0 075 184 * 3/1983 (EP) .
0 192 129 * 8/1986 (EP) .
0 244 873 * 11/1987 (EP) .
1092634 * 11/1967 (GB) .
63-036783 * 2/1988 (JP) .
88/00614 * 1/1988 (WO) .

* cited by examiner

Primary Examiner—William H. Beisner
(74) Attorney, Agent, or Firm—Clifford A. Poff

(57) ABSTRACT

A biological process is enhanced by a method and apparatus used to contact a biomass with a gas and with a nutrient liquid. A resiliently compressible porous matrix system containing the biomass is mounted in a reaction vessel containing a body of the nutrient liquid and a body of the gas above the body of the liquid. The body of liquid having an upper surface exposed to the body of gas and defining a liquid-gas interface. The resiliently compressible porous matrix system is located in a position in the reaction vessel so that compressible porous matrix system is partly immersed in the nutrient liquid and partly extends above the upper surface of the liquid into the body of gas. The mounting of the porous matrix system is used to rotate the system about a substantially horizontal axis such that a member or the location of the rotational axis relative to the reaction vessel acts on compressible porous matrix system causing periodic compression and expansion of regions of the porous matrix system without significant loss to the biomass.

42 Claims, 10 Drawing Sheets

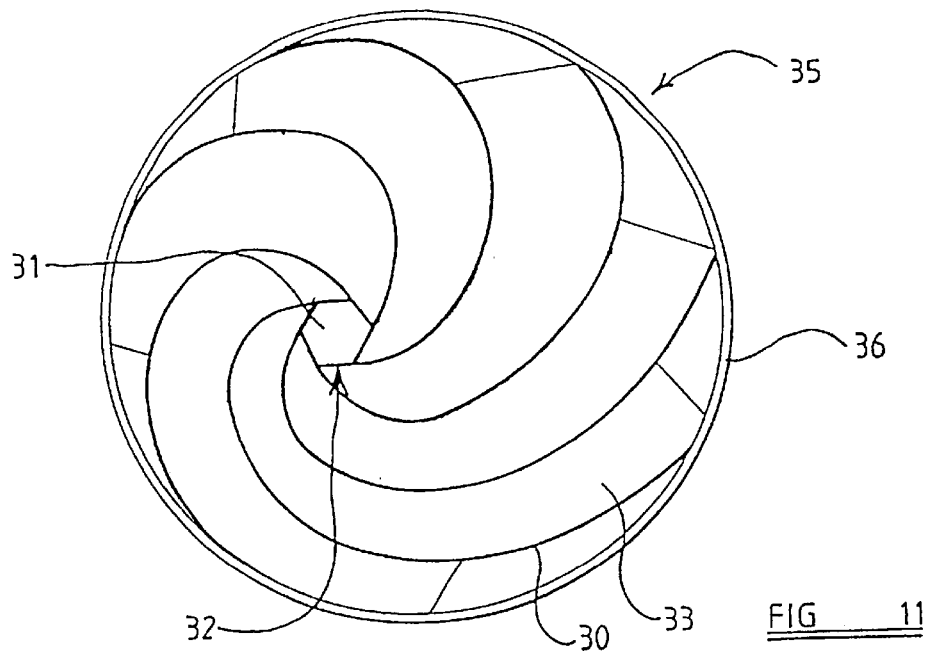
FIG 11
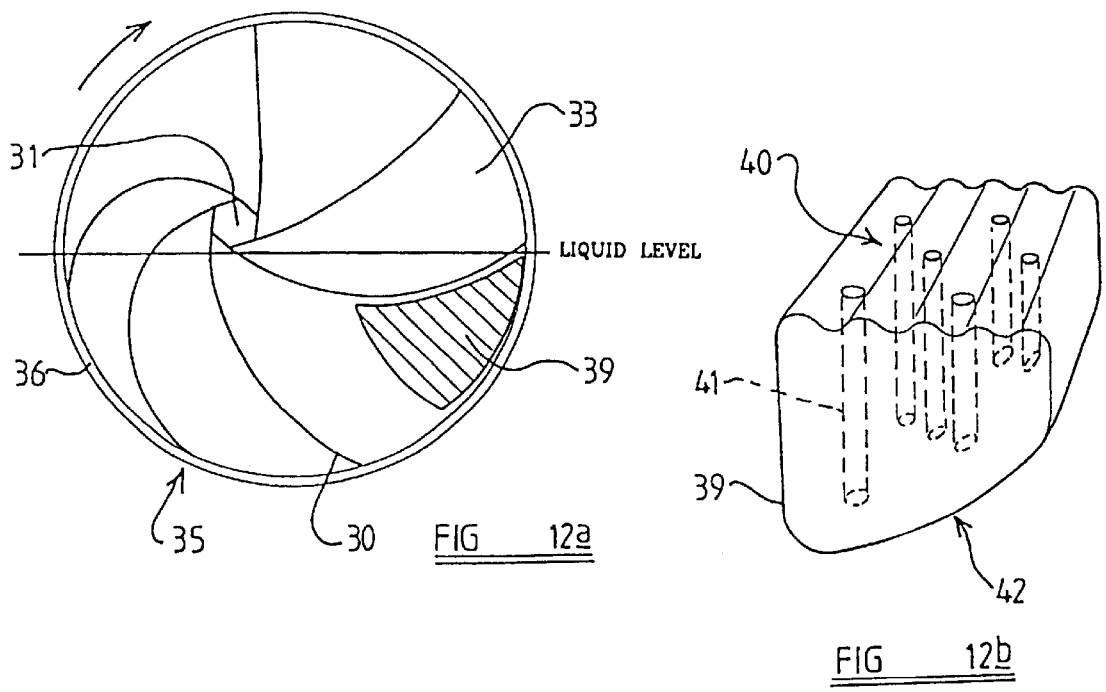
FIG 12a
FIG 12b

METHODS AND APPARATUS FOR ENHANCEMENT OF MASS TRANSFER OF A FLUID IN A POROUS MATRIX SYSTEM CONTAINING BIOMASS

This application is a continuation of International Application PCT/GB97/03179, with an international filing date of Nov. 19, 1997.

The present invention relates to methods and apparatus for the enhancement of mass transfer of a fluid in a porous matrix system and, more particularly, to methods and apparatus for the controlled enhancement of mass transfer of gaseous and liquid media into and out of a biomass-containing porous support medium.

The present invention also relates to the harnessing of microorganisms in controlled processes which use oil or petroleum as a substrate and, more particularly, to methods and apparatus which enhances mass transfer of a fluid in a porous matrix system containing said microorganisms, for use in such controlled processes.

In the past, man has cultivated microorganisms in a controlled manner to take advantage of the wide range of biochemical reactions which can be mediated by their presence in a defined growth environment. One of the most well established industries in this field is the so-called "fermentation industry", which today finds practical uses in, for example, brewing, baking and many other food and beverage processes. Since the end of the last century, man has harnessed microbes in controlled processes for the removal of pollutants from waste water and organic residues. The concept of using microorganisms for the removal of inorganic constituents from aqueous solution is also well documented and includes biosorption and luxuriant uptake. Microbes are also capable of bioconversion of some inorganic constituents, such as ammonia, via autotrophic nutrition. Also, in the field of fermentation technology, microorganisms and plant or animal cell cultures are now being extensively used to produce a wide range of chemicals and pharmaceutical products, with genetically engineered microorganisms and plant or animal cell cultures creating further interest in the biotechnology field.

Waste water and organic residue treatment processes both rely on contacting a mixed population of aerobic microorganisms with the waste water or organic residue to be treated in the presence of dissolved oxygen.

Biosorption is a general term applied to the removal of a range of constituents from solution by biological cellular material through both passive and metabolically active processes. Bioabsorption generally involves active transport across a cell membrane, whereas bioadsorption generally involves extra-cellular concentration of material at a cell surface and is not necessarily metabolically linked. Bioabsorption has been used successfully for the concentration of heavy metals from solution, including a wide range of radio-nuclides, which become concentrated in the cell. Such processes are generally aerobic and require the presence of organic growth constituents. The mechanisms used by certain microorganisms to concentrate inorganic salts across their cell membranes are of particular interest where these may be controlled to result in a net uptake of salt, with consequential decrease in the salinity of the medium which surrounds them.

Luxuriant uptake is a specific term applied to the bioabsorption by a microorganism of an essential element in quantities in excess of those normally required for metabolic processes. The prime example of luxuriant uptake is that of phosphorous removal from waste water in, for example, the so called "Bardenpho" and "Phostrip" processes.

Autotrophic nutrition by certain categories of microbes will result in the chemical transformation of inorganic constituents from one oxidation state to another, the two main examples being that of nitrification and sulphide oxidation. Such aerobic transformations of inorganic constituents may be beneficial to the final quality of water and are, thus, often practised in the treatment of waste waters or the treatment of sulphide rich gases in wet scrubbers.

The above processes, with the exception of bioadsorption and luxuriant phosphate uptake, all rely upon aerobic microbial reactions.

In the case of the production of chemicals and pharmaceutical products, the conditions of growth of the microbes or plant or animal cell cultures rely upon supply of appropriate nutrients, as well as aeration of the culture medium, in order to ensure that aerobic conditions prevail.

In all these processes, it is desirable to optimise the quantity of biomass in intimate contact with the particular medium concerned. Techniques involving biomass retention or biomass recirculation are useful, but will only be successful if it is ensured that the biomass is constantly supplied with the gases and nutrients required for growth and metabolism and, depending on the particular process involved, that the biomass is effectively supplied with a particular medium, or released products of metabolism effectively removed. There is, therefore, a desired to maximise biomass concentration per unit volume of reactive capacity, within the restraints of the mass transfer capacity of relevant gases and liquids into and out of the metabolising biomass, so as to minimize reactor size. (It should be noted that optimisation may well involve a compromise between maximising the biomass concentration per unit volume of reactor capacity and increasing the mass transfer of relevant gases and liquids into and out of the metabolising biomass. Too high a concentration of biomass per unit volume of reactive capacity, for example, could act against efficient mass transfer). Many techniques have, thus, been developed to enhance biomass retention and to improve mass transfer.

In particular, a wide range of specialist reactors have been developed for containing microorganisms or plant or animal cells during their growth and reaction periods and these vessels range in complexity from simple open vats to fluidised beds, which can be sterilised in preparation for use. Many of these reactors immobilise biomass on a porous support medium, such as open-celled foam, in order to maximise the surface area available for colonisation by the microorganisms or plant or animal cells and thereby increases the biomass density per unit volume of reactor. For example, the surface area available for colonisation by microorganisms, or plant or animal cells has been increased in packed column reactors by using a reticulated polyurethane foam as the support medium, and by either percolating the culture medium down through the bed of foam, or by causing the culture medium to flow upwards through the bed of foam. In such cases, however, control over the mass transfer of nutrients and gases to the biomass is governed only by the irrigation rate.

Another example where porous support media have been used to immobilise biomass is in rotating contact reactors aimed at maximising the surface area per unit volume, whilst maintaining a high proportion of void volume within the reactor bed. In such applications, the porous support medium, such as a substantially open-called foam, is attached to a rigid structure, usually in the form of a circular disc, which is rotated about its axis, with partial submergence in a trough of aqueous growth medium. Such a device alternately exposes the microorganisms or plant or animal cells to the nutrient medium and air in a manner that is controlled by varying the rotational speed of the device. On submergence of the porous biomass-containing matrix in the liquid phase, the interstitial spaces of the porous support medium are filled with the liquid medium to a point approaching saturation. When removed from the bulk liquid, the open pores of the medium will naturally drain their liquid contents, with a subsequent replacement of the drained void volume with air. In such a device, however, the only control exerted over the gravity induced mass transfer of liquid and gas from the porous elements is variation of rotational speed.

Other devices, in which the porous support medium is contained within a rotating drum, have also been proposed. Here, mass transfer of gas and liquid into and out of the fluid spaces in the porous support medium relies entirely upon gravitational forces and, again, the usual way of influencing mass transfer is by varying the rotational speed of the device.

In air-lift fermenters, biomass has been immobilised onto porous reticulated particles, the aim of which is to entrap the biomass within the reactor, thereby increasing the cell retention time. No special provision is, however, included in these systems to enhance mass transfer of gas or liquid into the pores of the support particles.

In mixed reactor systems, such as aeration tanks, reticulated porous support particles are again used in processes which serve to enhance the biomass concentration in contact with the liquid. However, no special provision is included to enhance mass transfer of gas or liquid either.

Waste water and organic residue treatment processes have both traditionally relied on two basic types of system, namely, 'fixed bed reactor' systems (biological filters), in which liquid occupies only a fraction of the bed volume, with much of the liquid being in thin film, and suspended growth systems (activated sludge), in which the biomass is surrounded by bulk liquid. Process modifications to the basic fixed bed reactor systems designed to increase biomass concentration per unit volume of reactor capacity, with increased mass transfer of gaseous and liquid fluids, include the rotating biological contactors mentioned above, biological aerated filters and a host of specially designed support media. Process modifications to the basic activated sludge processes include the use of pure oxygen in place of air; the deep shaft process; deep tank or tower reactors, fluidised beds with dissolved oxygen enhancement; the use of psuedo-fluidised beds with biomass support particles, such as in the "Captor" process; and the use of biomass support particles for biomass retention, such as in the "Linde" process. Many of these techniques, however, require complex plant and ancillary equipment making them often economically inefficient.

Furthermore, in the "Captor" and "Linde" processes for waste treatment referred to above and as disclosed in, for example, Patent Specifications Nos. GB-2111039 and U.S. Pat. No. 4,566,971, small pieces of foam are suspended and aerated in a liquid medium. These small pieces of foam allow the colonisation of the reticulated matrix by microorganisms whilst still maintaining direct access to the medium. This allows diffusion processes to take place, provided that the biomass film does not bridge strands of the supporting structure to such an extent as to cause blockage of the void spaces. In both processes, the colonised foam particles more relative to one another and, because of the relatively small size of the particles, inter-particle reaction will occur, generating frictional loss of the surface structure. To make the particles larger would minimise such frictional losses, but would also impede mass transfer of gases and aqueous media to the interior of the foam, i.e. would impose a greater diffusional limitation. If such diffusional limitation could be overcome, the particles could be larger, and possibly maintain static in relation to each other, thereby minimising frictional forces and subsequent attritional losses of the particles themselves. There is also the further problem that small pieces of foam tend to float to the surface of the liquid, particularly in the "Captor" process, and are then at risk of being blown away.

In the case of the production of chemicals and pharmaceutical products by microorganisms or plant or animal cell cultures, in order to improve the mass transfer of gaseous and liquid fluids to a metabolising biomass, a range of fermenter designs have been proposed and are used extensively in both laboratory and commercial work. Fermenters designed for aerobic cultivation induce oxygen transfer to the bulk liquid in a number of ways, the most common of which is by air or oxygen sparging into a well mixed reactor. Other techniques have been developed so as to reduce the shear forces induced by mechanical mixing and include the air-lift fermenters and packed tower reactors mentioned above, as well as shake flask techniques. Many of the techniques used in the chemical and pharmaceutical industries, however, being relatively harsh, may not provide optimum conditions for growth or metabolism and can seriously affect the viability of shear sensitive cells.

Thus, three is a desire to overcome, or at least obviate, the above-mentioned disadvantage and to provide a suitable and more efficient reactor design which would improve mass transfer of gases and liquid to and from the cell surfaces of a metabolising biomass, whilst at the same time allowing an increased biomass density per unit volume of reactor, thereby improving the overall rate of the particular reaction concerned.

According to the present invention, there is provided an apparatus for enhancing mass transfer of a fluid in a porous matrix system, which apparatus comprises a reaction vessel for containing a fluid medium, means for applying a series of controlled compressive forces to a region of the porous matrix system, each compressive force being releasable, in use, and effective to extrude fluid, but not significant biomass, contained in the porous matrix system and means for controllably expanding the region of the porous matrix system in the fluid medium following release of a compressive force.

Preferably, the reaction vessel contains, in use, first and second fluid media and the apparatus further comprises means for transferring the region of the porous matrix system from one fluid medium to the other between repeated expanding steps.

According to the present invention, there is also provided a method for enhancing mass transfer of a fluid in a porous matrix system, which method comprises the steps of (a) applying a controlled compressive force to a region of the porous matrix system, the compressive force being effective to extrude fluid, in use, but not significant biomass, contained in the porous matrix system, (b) releasing the compressive force, (c) controllably expanding the region of the porous matrix system in a medium containing said fluid and repeating steps (a) to (c).

Preferably, the method further comprises the step of transferring the region of the porous matrix system from one to another of first and second fluid media before repeating step (c).

The compressive force may either be applied in the direction of travel of the region of foam, in a direction which is perpendicular thereto, or a combination of both.

The mass transfer rate of both gaseous and liquid fluid to an actively metabolising biomass can, thus, be enhanced, over that which would normally be obtained by simple diffusion into and out of the porous matrix, gravitational drainage and/or irrigated blow, by means of the present invention, in which mechanical compression of a flexible support medium is followed by relaxation of the compressive force. This allows an expansion of the volume in the porous matrix, which fills up with gaseous or liquid fluid at a much greater rate than would otherwise be obtained by simple diffusion or relative movement between the biomass support and the fluid medium. This compression and expansion of a region of foam is advantageously achieved in the present invention without the need for complex internal mechanisms.

In the case, for example, of an aerobically respiring biomass, which requires a constant supply of nutrients from an aqueous growth medium, a system employing the basic principle of the present invention is likely to have alternate cycles of exposure to air (or an oxygen enriched atmosphere) and the aqueous phase. The controlled compression and expansion of the porous support matrix aids in the flow of the aqueous medium into and out of the biomass laden support medium, and this will aid in the mass transfer of soluble components of the aqueous phase, both into and out of the biofilm. In addition, the action will significantly increase the displacement of the aqueous phase, allowing enhancement of the gaseous phase uptake, so that the aqueous phase is cyclically expelled and gaseous intake cyclically induced. The basic principle of the present invention could be considered to be analogous to the familiar devices used in mammals to ensure their physiological success, i.e. the lungs, heart and circulatory systems.

According to one aspect of the present invention, an element or region of foam is, preferably, propelled through a closed loop path (which may be circular or even elliptical) and, during this circuit, the element of region of foam is passed through two zones where the element or region of foam is constricted. These zones are preferably contrived where the foam elements or regions enter and leave a liquid medium in a drum or trough (which has an influent fluid stream and an effluent weir when used as a continuous bioreactor, and which is provided with a gaseous medium above the liquid medium), i.e. at the interface between the first and second fluid media. In one preferred embodiment, the porous matrix system is in the form of a rotating foam biocontactor, with the foam divided into sectors, and with means provided for compressing the foam sectors as they enter or leave one or other of the fluid media.

During the passage of a foam element of region through the liquid and gaseous media, there should, preferably, be sufficient room for the foam element or region to relax fully after the compressing step in the fluid boundary region. Should the foam lose its ability to expand after compression, or should the porous material chosen not be resilient, the mechanism propelling the elements or regions of foam should, preferably, be able to expand the elements or regions of foam again, after compression. Thus, expansion may occur either as a result of the natural resiliency (decompressibility) of the porous support matrix exerting a restoring force, by way of an expansive force being applied thereto, or a combination thereof.

In any such systems, it is desirable that the liquid contact time should be no more than sufficient for biological uptake processes (i.e. "contact" delay) and the air contact time should not be prolonged into oxygen deficiency, which would result in a marked reduction in respiration rate. The duration of contact times should, therefore, be set accordingly. The aim is, preferably, to replenish or renew a thin but extensive internal film surrounding the microbes by means of a single pass of recently stirred medium through the matrix, followed by air or gaseous intake. Re-circulation of liquid within an area of the porous matrix once it has entered should be avoided as a waste of process time and the transitions between air and liquid contact periods should preferably be hastened, in the interest of efficiency, by local pumping within the porous matrix. Alternate squeezing and relaxation of the porous matrix system by the present invention achieves these aims and also enhances the effective use of reactive space. For each, in a container of fixed volume, within which a system of porous supports moves cyclically, the lower the proportion of space occupied with transport into and out of the biomass, the more remains for the productive metabolic stages and solute uptake. The distribution of the biomass in the system, the supply of its nutrient medium, the removal of soluble products, the access of oxygen and/or the efflux of gaseous products, are also made as even as possibly by the movement of the biomass support relative to the direction of liquid flow.

Thus, the present invention effectively brings design factors and local mass transfer limitations, such as the rate of fluid diffusion through different regions of a porous matrix system and unstirred layers of medium, into the operator's control. Mass fluid transfer into and out of the porous matrix system is efficiently enhanced, and local fluid circulation improved. This, and an increased concentration of biomass per unit volume of reactor, all serve to improve the overall rate of the reaction carried out by the microorganisms concerned.

A further advantage of the present invention is its relative compactness and low energy requirements, which make the present invention particularly attractive for applications where space and/or energy consumption are important considerations.

It should be noted that, in those examples of the present invention which use rotors in combination with a drive system almost all the energy of motion received from the drive system by the rotors is expended in bending members, compressing foam and moving fluids against frictional forces (depending, of course, on the materials used to construct the rotor, one suitable material, in this respect, being, for example, fibre-reinforce plastic). Because of the thin film nature of the contact, all these movements are more effective than, the example, processes involving sparging and stirring (in which large volumes of gas and liquid are moved without being fully equilibrated with one another).

Whilst the apparatus of the present invention is particularly suitable for the treatment of organic residues such as animal slurries and waste water treatment, there is a very wide range of other potential uses to which the present invention may be applied. These include, for example, the aerobic biodegradation or organic pollutants; the production of microbial products; and the removal of inorganic components from aqueous solutions by metabolically linked absorptive processes. Thus, the present invention has potential for use in the fermentation industry, for aerobic cultivation of microorganisms or plant or animal cell cultures, for the production of host products including antibiotics, food products and biochemical compounds; in the genetic engineering field; and in water treatment, for the reveal of salts in microbially mediated desalination processes and for the removal of metals, including radio-nucleotides, from both raw and uses waters. Possible application of the present invention is envisaged in, for example, bakeries, breweries, landfill sites, pig farms, pharmaceutical plants, agricultural units, ships, camp sites and other utility and service areas. In addition, devices according to the present invention could be used for purification of raw water from lakes, reservoirs, rivers and possibly more slaine sources of raw water, where there is a requirement to remove inorganic components.

In addition to the above-mentioned uses, which list is by no means exhaustive, the apparatus and method of the present invention also have important and far-reaching uses in the petroleum industry, as described in more detail herein.

Thus, in accordance with another aspect of the present invention, there is provided a method for metabolising or degrading an oil or petroleum hydrocarbon, or an oil or petroleum-derived product, or for metabolising or degrading a contaminant of oil or petroleum or an oil or petroleum-derived product, which method comprises loading a porous matrix system with a suitable microorganism, submerging the porous matrix system, at least partially, in a fluid containing the oil or petroleum hydrocarbon, oil or petroleum-derived product, or contaminant, and (a) applying a controlled compressive force to a region of the porous matrix system, the compressive force being effective to extrude fluid, in use, but no significant biomass, contained in the porous matrix system, (b) releasing the compressive force, (c) controllably expanding the region of the porous matrix system in the fluid, and repeating steps (a) to (c).

The relative compactness and low energy requirements also make the apparatus and method of the present invention particularly suitable for use in the petroleum industry.

It will, of course, be appreciated that the potential range of uses of the present invention will increase as further uses for microorganisms, or plant or animal cell cultures, are discovered or developed.

In many of the above-mentioned uses, both economic and environmental considerations will, of course, apply in their application, and various regulations may be in force limiting the use of the present invention in certain cases. Thus, for example, an embodiment of the present invention which is ideally suited for treating highly concentrated slurries for discharge to sewer may not meet the standards for all water usage categories. Because of the low energy requirements and the potential application to a range of polluted water types, however, the invention may find application in other countries, such as third world countries, for the treatment of polluted waters to a standard suitable for domestic or agricultural purposes. Thus, whilst the present invention may be more suited to particular uses in the western world, the present invention may be applied to a wide range of other uses in targeted areas in third world countries, and the many advantages of the methods and apparatus of the present invention may be of particular interest to the World Health Organisation.

Whilst particularly suitable for aerobic processes, it should be noted that the methods and apparatus of the present invention are applicable to both aerobic and anaerobic processes and have the potential to be applicable to any viable biomass in which there is gas intake, gas output or both, or where a regular supply of fresh liquid media to the biomass is required. The methods and apparatus of the present invention also have the potential to be applicable to non-viable biomass used for the purposes of bioadsorption.

In order that the invention may be more readily understood, and so that further features thereof may be more readily appreciated, examples of the invention will now be described, by way of example only, with reference to the accompanying drawings, in which:

FIG. 7b shows a diagrammatical plan view of the example of the apparatus shown in FIG. 7a;

FIG. 11 shows a diagrammatical front view of part of an apparatus according to an eighth example of the present invention;

FIG. 12a shows a diagrammatical front view of part of an apparatus according to a ninth example of the present invention;

FIG. 12b shows a diagrammatical perspective view of the float of FIG. 12a; and

Figure 1:
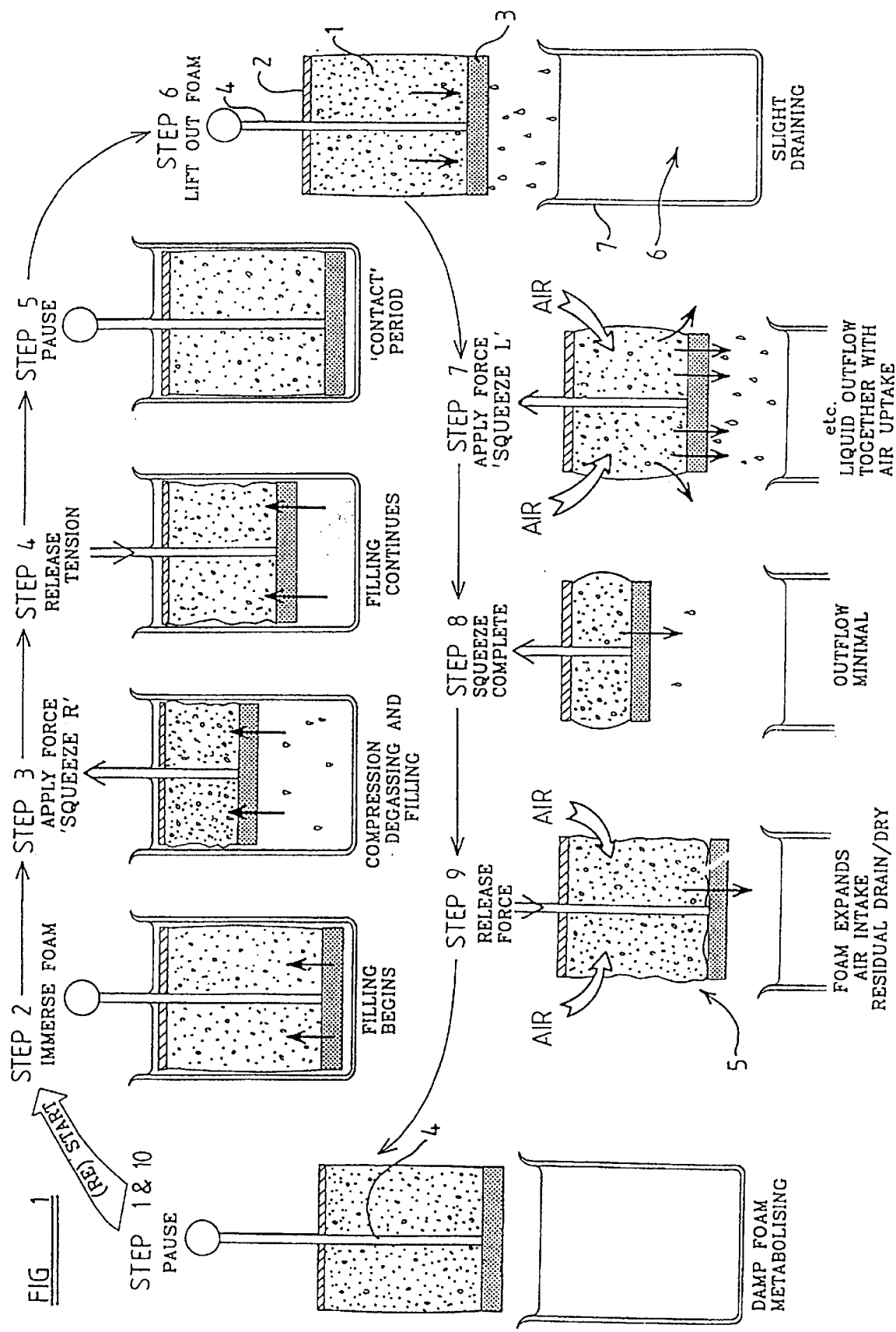
FIG. 1 shows a sequence of steps involved in a first example of the present invention.

FIG. 1 of the accompanying drawings shows a first example of the present invention in the form of a model to demonstrate the operational principle of the present invention. This example uses a compressible and resilient cylinder of reticulated polyurethane foam 1, approximately 97% void, and loaded with viable, metabolically active, bacterial cells in small clusters or piles (not shown) which adhere to the *rami* or *trabeculae* (not shown) of the foam. The foam cylinder 1, is held between an upper disc 2, which is impermeable to water and a lower, permeable, disc 3. The upper 2 and lower 3 discs are connected by a central rod 4, the lower end of which is attached to the lower disc 3 and the upper end of which passes through a hole (not shown) of a central portion (not shown) in the upper disc 2. By pulling the central rod 4 through the hole in the upper disc 2, the lower disc 3 can be pulled towards the upper disc 2, thereby compressing the foam cylinder 1 therebetween.

Many types of at least partially open-celled foam which are standard in the industry would be suitable for use in this example of the present invention, and the foam may be inoculated with bacterial cells, or other microorganisms, by any suitable, conventional means.

As can be seen from FIG. 1 of the accompanying drawings, the method consists of a sequence of steps which cycle between a gaseous phase and a liquid phase. In step 1 of FIG. 1, the foam cylinder 1 is held in a gaseous medium 5 (such as air) above a liquid medium 6 (such as a nutrient medium or liquid to be treated), with the foam cylinder 1 in an uncompressed, naturally expanded, resisting state.

In step 2 of FIG. 1, the foam cylinder 1 is inserted into a cylindrical pot 7 containing the liquid medium 6 and into which the foam cylinder 1 fits exactly. As the foam cylinder 1 is inserted into the pot 7, a few gas bubbles (for example, air) will escape from the void spaces in the foam and will be replaced by liquid from below.

In step 3 of FIG. 1, the central rod 4 is pulled upwardly so that the lower disc 3 is pulled towards the upper disc 2, thereby compressing the foam cylinder 1 between the discs 2,3. The compressive force applied is substantially in the direction of insertion of the foam cylinder 1 into the cylindrical pot 7 and this compresses the foam to a degree short of extruding a paste of concentrated biomass (which would require a greater applied force). The foam is degassed, mainly as a consequence of hydraulics, the rate of degassing being enhanced by compression of the foam.

In step 4 of FIG. 1, the tension on the central rod 4 is released, thereby allowing the foam cylinder 1 to expand, with further ingress of liquid from the liquid medium 6 into the de-gassed foam spaces.

Step 5 of FIG. 1 involves a pause, in which the foam cylinder 1 is allowed to remain at its rest volume, whilst metabolic processes associated with the microorganisms occur. This may be described as the "contact" phase of the immersion cycle.

In step 6 of FIG. 1, the foam cylinder 1 is lifted out of the pot 7 again so that liquid begins to drain out of the foam cylinder 1 and back into the pot 7 under gravitational force. A small amount of gaseous fluid (e.g. air) is able to enter the drained void spaces of the foam at this stage.

In step 7 of FIG. 1, force is again applied between the two discs 2, 3 to compress the foam cylinder 1 therebetween and this greatly accelerates extrusion of liquid from the foam cylinder 1. The compressive force applied is substantially in the direction of transfer of the foam cylinder 1 from the liquid to the gaseous medium and compression continues in step 8 of FIG. 1 until the rate of further draining is not significantly responsive to further compression (i.e. until liquid outlow is minimal). The tension on the central rod 4 is then released in step 9 of FIG. 1, so that the foam cylinder 1 is able to expand back again to its natural resting state. The foam cylinder 1 is still held above the pot at this stage and expansion of the foam cylinder 1, thus, accelerates ingress of gaseous fluid into the drained void spaces.

In step 10 of FIG. 1, which is also step 1 of the cycle, the damp foam cylinder 1 is allowed to remain at its rest volume, during which gas exchange takes place within the interstices of the foam. After a set period of time, the foam cylinder 1 is then re-inserted into the pot 7, as in step 2 of the cycle, and the cycle repeats.

It should be noted that step 3 (the de-gassing step) may precede step 2 in the example of FIG. 1, whereby compression and de-gassing of the foam is carried out before immersion into the liquid medium 6.

The cycle of FIG. 1 may, of course, be mechanised and used, for example, by way of repetition, for a batch fermentation to make a product, after innoculation of the medium with a suitable microorganism, which would be trapped in, and bound to, the foam. This example of the present invention would be particularly suitable for chemical and pharmaceutical applications, because the mechanisms employed provide a relatively gentle environment for growth of the microorganisms and may easily be adapted to provide sterile conditions. Cells may also be easily discharged or harvested in this example of the present invention, for example, by applying an increased compressive force so as to extrude biomass as a paste. The liquid flow in this example of the present invention is, however, uni-directional and the conditions at the top of the foam cylinder 1 are unlikely to be the same as at the bottom of the foam cylinder 1, which may be a cumulative disadvantage after a number of cycles.

Figure 2:
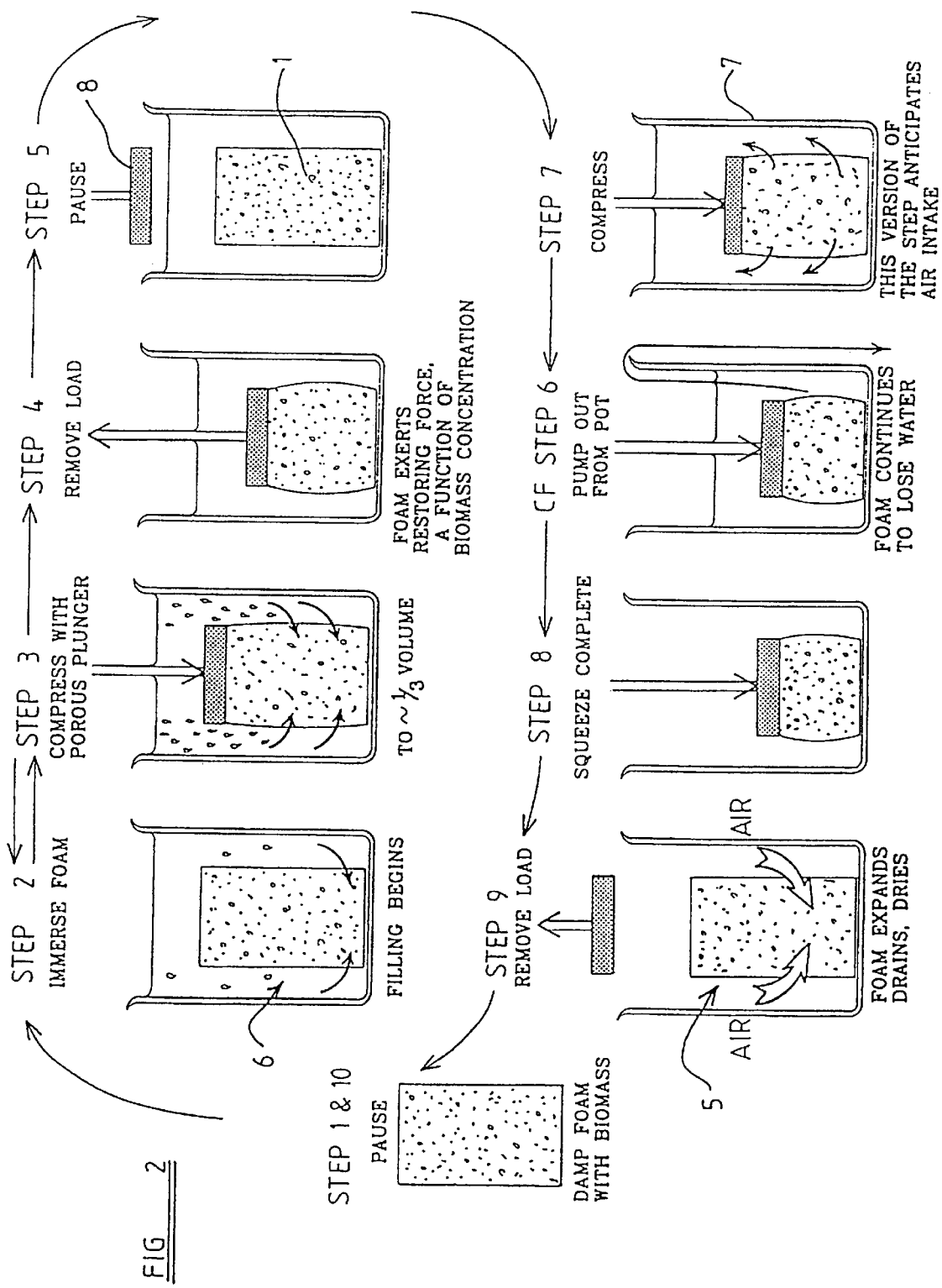
FIG. 2 shows a sequence of steps involved in a second example of the present invention.

A second example of the present invention may be seen in FIG. 2, and is an improvement over the first example of FIG. 1, in that a free space is provided around the foam cylinder 1 between the edge of the foam cylinder 1 and the walls of the pot 7 to allow liquid circulation and mixing, so that the flow pattern now becomes essentially two-dimensional. Other differences between the examples shown in FIGS. 1 and 2 is that, in the example shown in FIG. 2, the foam cylinder 1 is not held between a pair of upper 2 and lower 3 discs, but is instead compressed by means of a porous plunger 8 which is applied to an upper surface of the foam cylinder 1 whilst a lower surface of the foam cylinder 1 lies against the bottom of the pot 7. The exact sequence of steps in FIG. 2 also differs slightly from these shown in FIG. 1, in that, for example, steps 6 and 7 are reversed so that the foam cylinder 1 is compressed whilst still immersed in the liquid medium and the liquid medium then removed from the pot 7 (i.e. pumped out) to allow draining of the liquid, rather than the foam cylinder 1 first being removed from the pot 7 and then compressed, as in FIG. 1 of the drawings. The removed liquid would subsequently be returned to the cycle. Also, as in FIG. 1, step 3 may, again, precede step 2.

Figure 3:
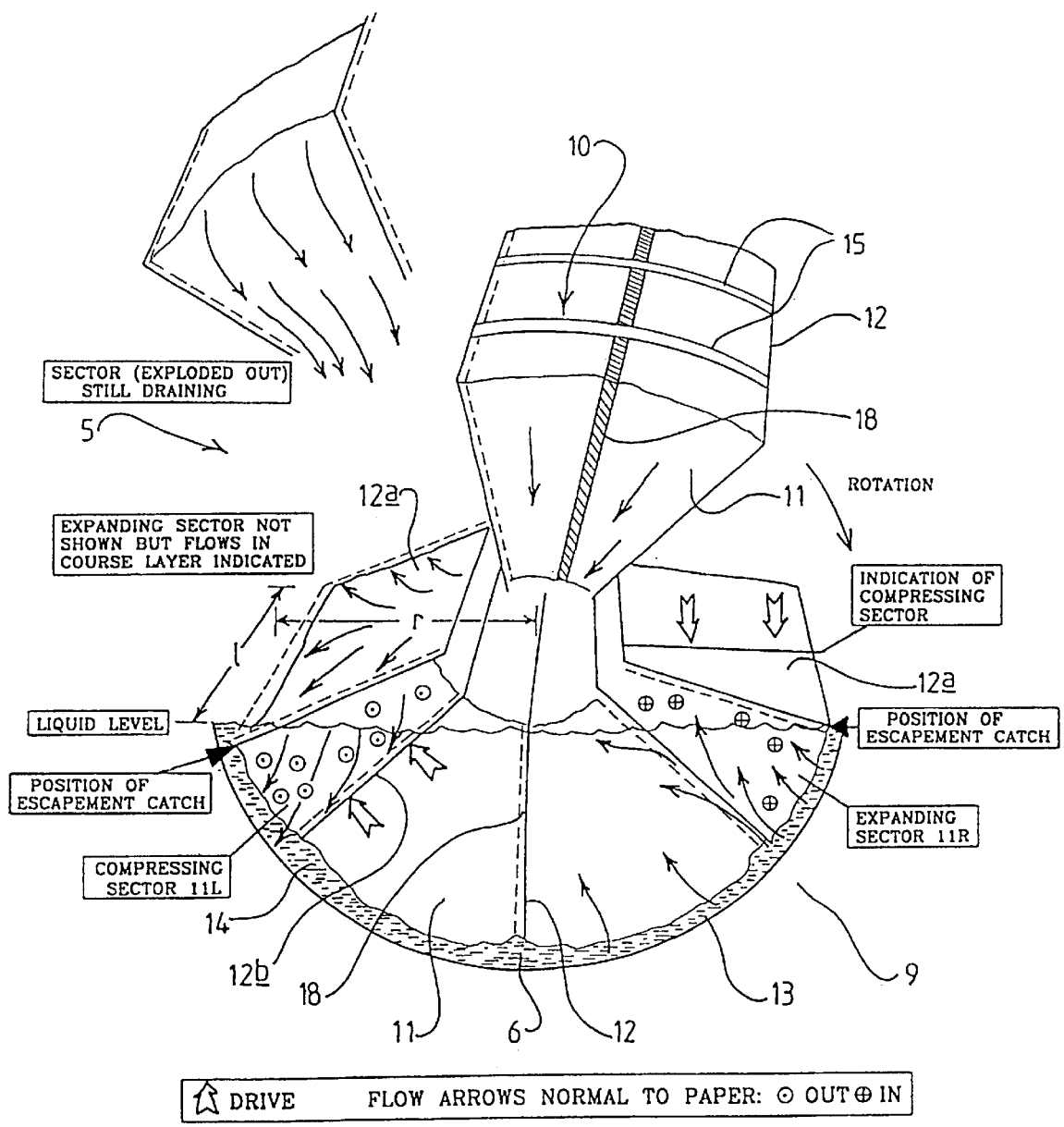
FIG. 3 shows a diagrammatical perspective view of part of an apparatus according to a third example of the present invention.

FIG. 3 of the accompanying drawings shows a third example of the present invention which may be described as a rotating sectored foam biocontactor 9. This example of the present invention allows a simplified control over the enhancement of mass transfer of liquid and gases in the foam matrix and provides a process which may be easily and economically mechanised.

The rotating sectored foam biocontactor 9 shown in FIG. 3 is a composite cylindrical structure comprising a plurality of annular foam sub-units 10. The foam of adjacent sub-units 10 is separated in the axial direction by approximately two centimetres, and this space may be filled with a coarser foam or another suitable layer of coarse material (not shown), such as an open woven filamentous material or melt-blown plastic mesh. The sub-units 10 are linked mechanically in the axial direction so that each sub-unit may be driven at the same rotational speed. Each foam sub-unit 10 is divided into nine equal sectors 11 and each foam sector 11 is separated from the next by a waterproof rigid barrier or radial septum 12.

The rotating sectored foam biocontactor 9 is driven by a rotor (not shown) about its axis and rotates (in this example of the present invention, in a clockwise direction) in a trough 13, the profile of which is part of a circle. The trough 13 contains liquid medium 6 of a depth sufficient just to wet each foam sector 11 as it passes through the trough 13. (The level of the liquid medium 6 in the trough 13 may, of course be varied as desired, and according to any particular needs with regard to the ratio of foam/biomass to liquid). The foam sectors 11 do not actually contact the bottom of the trough 13, but are separated from it by a small annular space 14, for example, approximately 3.5 cm deep; for circulation and mixing of the liquid medium 6. Tumbling of the foam sectors 11 into and out of the liquid medium 6 at the same time helps to aerate the liquid medium 6.

Whilst it is not necessary to the principle of the present invention, it is preferable, for other reasons, that the trough 13 is part of a complete circular cylinder (not shown) which defines and protects the reactor space.

The rotor (not shown) may be driven by any conventional means and a rotor drive (not shown) may be connected to each end of the linked sub-units 10. Mechanisms (not shown) are provided so that, at any given point, the rotor drive acts on a pair of opposing septa 12, thereby pushing one foam sector 11 on one side of the rotating sectored foam biocontactor 9 into the liquid medium 6 and another foam sector 11 on the other side of the rotating sectored biocontactor 9 out of the liquid medium 6 into the surrounding gaseous medium 5, so that a foam sector 11 is alternately exposed to the liquid medium 6 (for example, an aqueous nutrient medium or a liquid to be treated) and the gaseous medium 5 (for example air).

Two septa 12a immediately ahead of each of two driven septa 12b are held for a time from moving, as the biocontactor 9 continues to rotate, by escapement catches (not shown) on either side of the rotating bicontactor 9. This causes the foam sector 11 between the driven septa 12b and held septa 12a, on either side of the rotating biocontactor 9, to be compressed and this correspond functionally with steps 3 and 7 in FIGS. 1 and 2 of the accompanying drawings. Where a foam sector 11 is being driven into the liquid medium 6, on one side of the rotating biocontactor 9 (the right hand side in FIG. 3), compression of the foam sector 11 serves to de-gas the foam sector 11, and where a foam sector 11 is being driven out of the liquid medium 6 on the other side of the rotating biocontactor 9 (the left hand side in FIG. 3), into the surrounding gaseous medium 5, compression of the foam sector 11 serves to drain the foam sector 11 of liquid again. The compressive force, which, in this example of the present invention, is applied substantially in the direction of travel of the foam sectors 11, is sufficient to de-gas or drain the foam sector 11 in each case, but is not sufficient to extrude excess biomass. The escapement catches may be of any conventional type and may, for example, be triggered to release the septa 12a when a maximum desired compression of the foam sectors 11 is reached.

Following the compression steps, the escapement catches on either side of the rotating bicontactor 9 are released and the released foam sectors 11 immediately begin to expand. This corresponds functionally with steps 4 and 9 in FIGS. 1 and 2 of the accompanying drawings. The rotor continues to move, initially from its own momentum, but almost immediately thereafter, by engagement of the rotor drive mechanisms with the next approaching pair of septa 12. This is followed instantly by engagement of the escapement catches with the previously driven septa 12b, so that the next foam sectors 11 will be compressed. This sequence of events then repeats.

The rotating biocontactor sub-units 10 in this example of the present invention may be made from any suitable type of at least particularly open-celled foam, which may be standard in the art, for example, a compressible and resilient, reticulated polyurethane foam. A foam which is particularly useful for waste water treatment is specified by the parameter 30 pores per inch (11.8 pores per cm), although this measure is functional rather than dimensionally precise. Each sub-unit 10 preferably contains a total volume of foam which, it its relaxed state, is more than the space available. This is because, at any time, two of the foam sectors 11 are being compressed, and two in the process of returning to their rest volume, and has the additional desirable effect that energy from expanding the sectors 11 contributes to the onward motion of others. Inoculation of the foam with microorganisms may, again, be carried out by any suitable means.

Because the decompressibility of reticulated foam may decrease during its working life, or because a non-resilient or non-decompressible porous material may be preferred for a particular application, the foam sectors preferably have incorporated therein inextensible but flexible strips bridging the gap between pairs of septa 12. These flexible strips help to prevent the septa 12 from exceeding their design angles (or degree of separation) and prevent the foam from sagging. These flexible strips may for example, be in the form of perforated nylon belts or straps 15 an may be provided around the circumference of each sub-unit 10 and/or threaded through, or sandwiched between, layers in the foam. The flexible strips may alternatively, be in the form of stainless steel springs (not shown) embedded in the foam. The prevention of foam sagging may also be aided by the provision of peripheral buoyant foam inserts (not shown).

Where a non-resilient or non-decompressible porous foam is used in this example of the present invention, the flexible belts or straps 15, or stainless steel springs, could be configured so as to expand the foam sectors 11 following the compression steps, or simply aid expansion following release from the escapement catches in the case of resilient foam.

The diameter of the rotating foam sectored biocontactor 9 shown in FIG. 3 and, within limits, the number of sectors per subunit and the number of subunits per trough may, of course, be varied according to the particular use to which the biocontactor 9 is to be applied. For example, a rotating foam sectored biocontactor 9 having a radius of approximately 1–2 m (from the edge of the foam to the central rotational axis) and comprising six sub-units 10, each having a width of approximately 0.75 m in the axial direction, provides an advantageously compact system which is particularly useful for the treatment of organic residues such as pig slurries.

If each foam sector 11 in a biocontactor 9 having the dimensions mentioned above is compressed to about 25% of its rest volume in 15 seconds, the liquid extruded through the sides and curved end of the foam sector 11 is approximately 425 litres, which implies a linear velocity on exit of about 4 cm/sec. Because of this very high flow rate of draining liquid from the foam sectors 11 of the rotating biocontactor 9 in FIG. 3 of the accompanying drawings, it is preferable to divide the foam sectors 11 into blocks or sections 16, by providing a hierarchy of drainage lamina graded in their flow capacity as they progress downstream in the direction of fluid flow, so as to shorten the path for fluid drainage out of the foam. This is particularly important in rotating biocontactors having a radius of over 2 metres.

In order to aid flow of liquid through the foam sectors 11, and to prevent uneven drainage and liquid logging in the almost triangular section of each foam sector 11 during the compressing and draining steps, each foam sector 11 may, further, be provided with a plurality of radial flow channels, including a pair of radial flow channels adjacent each dividing septum 12. Because liquid viscosity is much greater than gas, it is preferable that gravity should reinforce the imposed squeeze which expels liquid. It is, therefore, preferable for the liquid-proof septa 12 below the direction of fluid drainage (i.e. the trailing septum in the direction of the rotation of a particular foam sector which is emerging from the liquid medium) is provided with a flow channel to take the expected flow without appreciable resistance that would lead to liquid logging.

Figure 4:
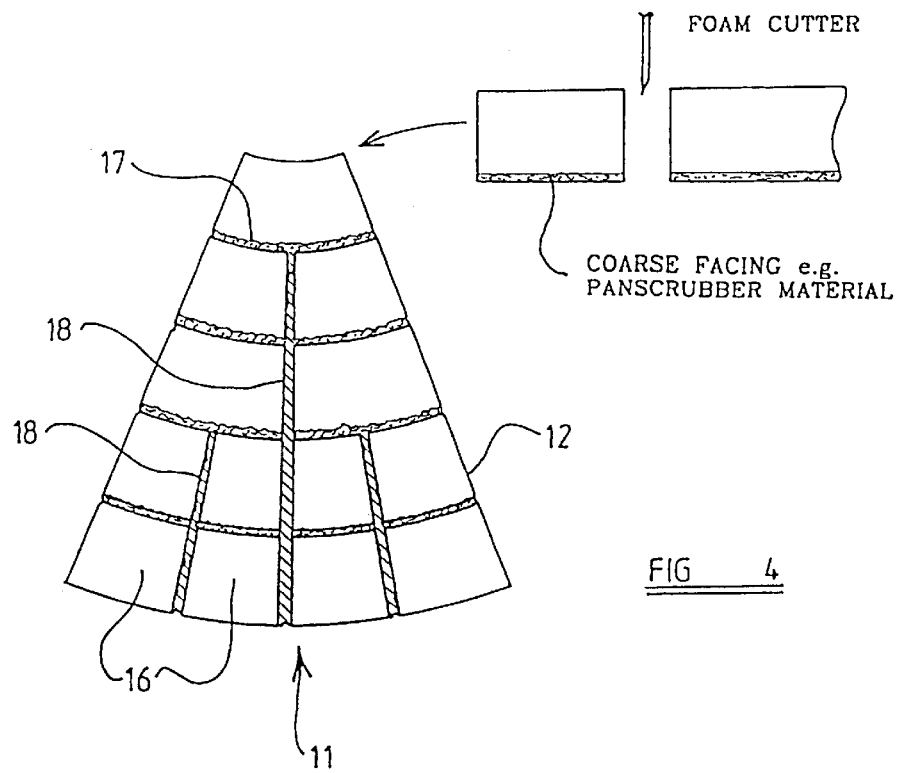
FIG. 4 shows a diagrammatical cross-sectional view of a single foam sector of FIG. 3.

In the example shown in FIG. 4 of the accompanying drawings, a foam sector 11 is divided into blocks 16 by a plurality of coarse facings 17 arranged as a series of concentric arcs about the central rotational axis of the biocontactor 9, and a plurality of radial inserts 18 forming flow channels, which extend to varying extents from the outer circumference of the sector 11.

In choosing the material for the coarse facings 17 which make up the drainage lamina, the question of linear flow velocity and the possibility of growth of microorganisms causing clogging will need to be considered in different applications. An open woven filamentous material such as a melt-brown plastic mesh may, for example, be suitable in certain circumstances. In the case of the flow channels 18, these must have smooth surfaces, as must the septa 12, to prevent attachment and growth of microorganisms thereon causing clogging, and may be formed, for example, from open polyvinyl chloride matting or semi-rigid corrugated polyvinyl chloride sheet, or a much more coarse and imcompressible foam than that of the sectors 11. Because such coarse layers will have neither the same wear or resiliency (de-compressibility) as the foam of the sectors 11, such coarse layers should, preferably, not be arranged along the direction of the compressive force, but should rather, be arranged perpendicular to the direction of the compressive force.

The example of the present invention shown in FIG. 3 has the advantage over the examples shown in FIGS. 1 and 2 that the direction of liquid flow, whilst not exactly specifiable, is generally 3-dimensional. The precise flow directions in the foam will, of course, depend on the concentration and spread of biomass within the foam. For example, if a piece of reticulated polyurethane foam (not shown) is filled with water and then squeezed from the top of two sides, water will effectively run out of the foam from the bottom only. However, if the foam is well filled with biomass, for example, at a concentration of 8 gms dry weight per litre, squeezing the foam will give a much slower efflux and a greater proportion of the water will escape from the sides of the foam. The biomass, which fills much of the void spaces in the foam, immobilises a substantial quantity of water within the foam and reduces the spaces and apertures available, thereby increasing resistance to flow so that the vertical force of gravity is relatively small, compared with the forces spread out in three dimensional resulting from squeezing the laden system. Thus, it is important that biomass be evenly distributed within each foam sector 11, particularly to prevent regions developing where mass transfer of gaseous or liquid fluid to and from a high concentration of cells is hindered.

Figure 5:
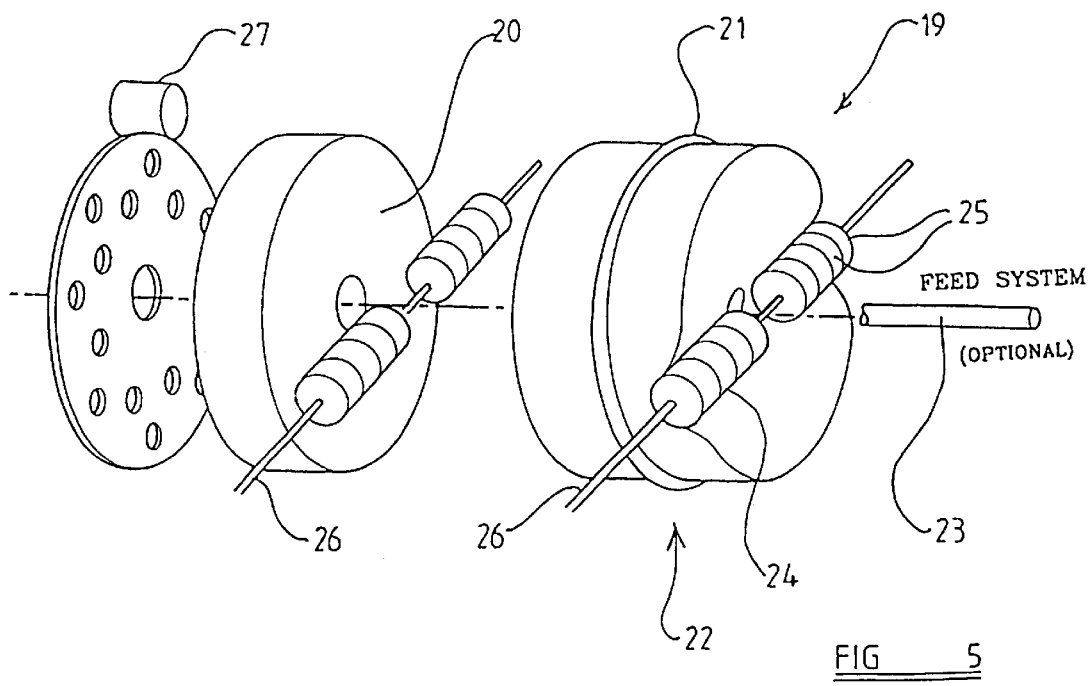
FIG. 5 shows a diagrammatical perspective view of part of an apparatus according to a fourth example of the present invention.

A fourth example of the present invention is shown in FIG. 5 and this example of the present invention is again in the form of a rotating disc biocontactor 19. As can be seen from FIG. 5, the rotating biocontactor 19 in this example of the present invention comprises a plurality of circular foam discs 20 which are secured to either side of each of plurality of circular rigid discs 21 to form a plurality of composite units or disc structures 22. The rigid discs 21 are perforated to allow flow of fluid therethrough and any suitable type of at least partially open-celled foam may be used for the foam discs 20, for example, a compressible and resilient, reticulated polyurethane foam. Inoculation of the foam with microorganisms may, again, be carried out by any suitable means.

The composite disc structures 22 are mounted for rotation about a central axial shaft 23 and the central axial shaft 23 is preferably hollow and perforated to act as a liquid inlet. Along the axis of rotation, the disc structures 22 alternate with rollers 24. Each roller 24 comprises a sequence of plastic bobbins 25 of equal radii, arranged on either side of the central axial shaft 23 of the disc structures 22, and rotatably mounted on a roller spindle 26. The roller spindle 26 is mounted horizontally in use, substantially in a diametric plane of the composite disc structures 22, with the rotational axes of the bobbins 25 perpendicular to the common rotational axis of the disc structures 22. Drive means 27 is provided at the edge of at least alternate rigid discs 21 for driving alternate disc structures 22 in opposite directions. Thus, either alternate disc structures 22 are driven in one direction, with intervening disc structures 22 acting as passive followers in the opposite direction through the perpendicularly arranged rollers 24, or alternate disc structures 22 are each driven in opposite directions. The rollers 24, which are not themselves driven, act as passive followers of the driven disc structures 22 and, as can be seen from FIG. 5, the bobbins 25 on one side of the central axial shaft 23 will rotate in the opposite direction to the bobbins 25 on the other side of the central axial shaft 23 in any particular roller, in line with the direction of the rotational forces exerted by the rotating disc structures 22.

The rotating biocontactor 19 of FIG. 5 of the present invention is, again, provided in a trough 13, the profile of which is part of a circle. The biocontactor 19 is partially submerged in a liquid medium 6 contained in the trough, and the rollers 14 are arranged to lie horizontally at, or near to, the liquid/gas interface.

The composite disc structures 22 and perpendicularly arranged rollers 24 are arranged sufficiently close to each other for the rollers 24 to apply a compressive force against the disc structure 22 and thereby squeeze the areas of foam in contact with the rollers 24, between the rollers 24 and the rigid discs 21, as the disc structures 22 rotate. The rollers 24 of FIG. 5, thus, act in place of the rotor drive and escapement catches (not shown) of FIG. 3 to compress regions of the foam discs 20 as they enter and exit the liquid medium 6 and the compressive force in this example of the present invention is applied in a direction which is substantially perpendicular to the direction of travel of the foam. The squeezing action corresponds functionally with steps 3 and 7 in FIGS. 1 and 2 of the accompanying drawings, and serves to de-gas the foam on entry into the liquid medium 6, and to extrude liquid from the foam on exit from the liquid medium 6. Once a particular region of foam has rotated past a particular roller 24 following the compression step, this region of foam will expand again due to the natural resiliency or decompressibility of the foam. This, again, corresponds functionally with steps 4 and 9 in FIGS. 1 and 2 of the accompanying drawings.

The example of the present invention shown in FIG. 5 is useful for applications in which cells need to be harvested or discharged from the foam, because this can be achieved by reducing the spacing between the rollers 24 and disc structures 22 until the rollers 24 exert an increased compressive force on the foam to extrude biomass as a paste.

Figure 6A:
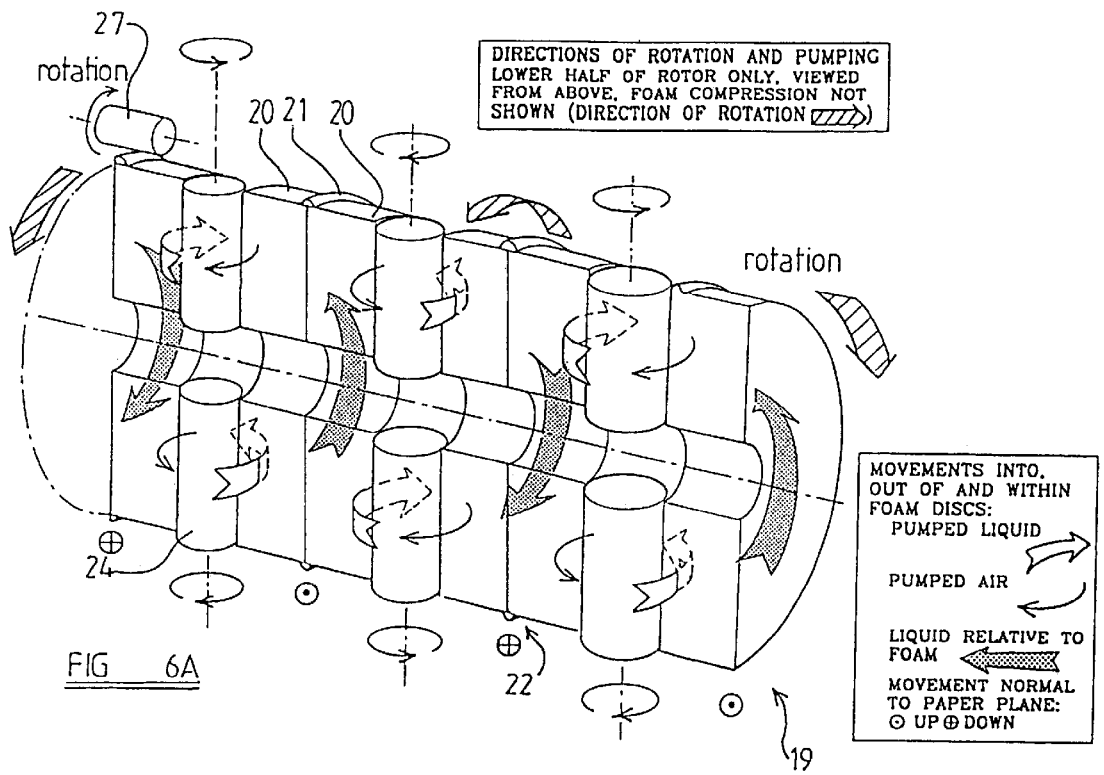
FIG. 6a shows a diagrammatical part-sectional, top plan view of the example of the apparatus shown in FIG. 5.
Figure 6B:
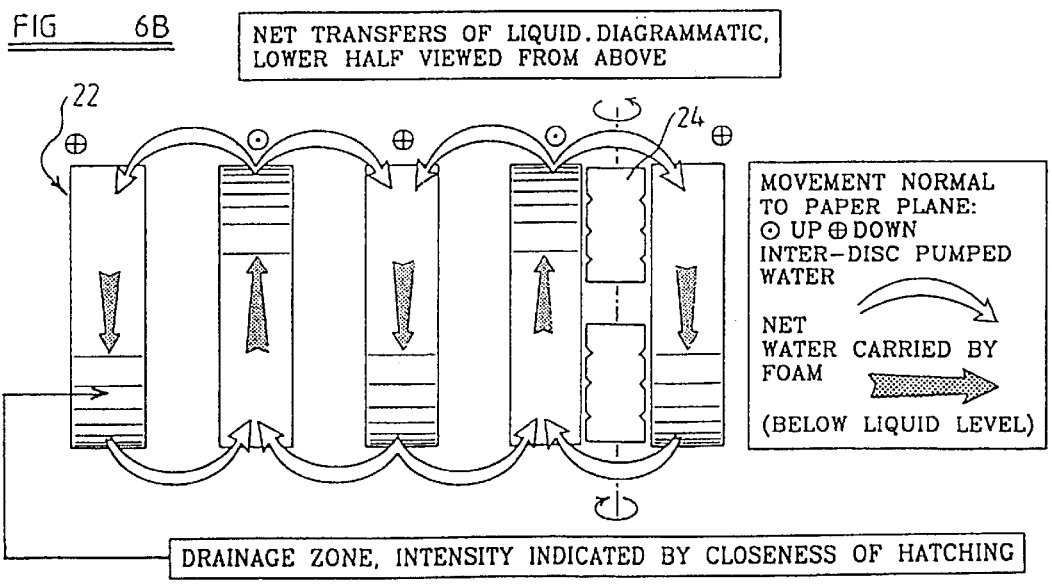
FIG. 6b is a diagrammatical illustration of flow patterns in the example of the present invention shown in FIGS. 5 and 6a, viewed from above.

Flow patterns of the liquid medium 6 in the example of FIG. 5 are diagrammatically illustrated in FIGS. 6a and 6b of the accompanying drawings. As can be seen, the flow pattern is generally 3-dimensional. FIG. 6b provides a clear illustration of the advantageous local circulation of liquid medium 6 that takes place between the foam discs 20 in FIG. 5, thereby bringing freshly mixed liquid medium to the biomass (not shown) in each cycle. This local circulation also takes place in the device of FIG. 3, in the annulus of liquid 14 between the edge of the foam and the trough 13.

With reference to FIGS. 6a and 6b, and as explained previously, for each rotating foam disc 20, gaseous fluid is, in effect, being pumped out by the rollers 24 as the foam enters the liquid medium 6 and, on the other side of the trough 13, liquid fluid is, in effect, being pumped out of the foam by the rollers 24 as the foam emerges from the liquid medium 6. In the steady state, there is, therefore, a greater amount of liquid in the submerged part of a foam disc 20 than above the liquid medium 6. To maintain this steady state, there must be a circuit of liquid transfer, whereby each foam disc 20 carries liquid contained in the foam in its direction of submerged motion and releases some of the contained liquid on emerging from the liquid medium 6. The difference between the liquid content per unit volume of foam and the volume of liquid pumped out per unit volume of foam at the point at which the foam emerges from the liquid medium 6 will be the net liquid transfer by the submerged part of the foam disc 20 from entry to exit from the liquid medium 6. Where gaseous fluid is pumped out, liquid fluid is drawn in to replace it, marking the other end of the external circuit. The remaining component of flow comprises pumped liquid fluid which does not leave the foam but which, instead, passes back along the foam as a result of the pressure applied by the roller 24 against the side of the foam disc 20 as the foam emerges from the liquid medium 6. This back-flow may comprise up to 30% of the pumped liquid and is in a direction which is opposite to the direction of the bulk-movement of liquid carried with the foam disc. From this, it can be seen that there will always be liquid inside the submerged part of the foam disc 20 which will move with respect to the foam matrix in the contrary direction to the rotation of the foam disc 20. The relative motion of this pumped intralayer circulation is sufficiently rapid to bring freshly mixed liquid to the microorganisms in each cycle. In addition, the released component of the liquid fluid from one foam disc 20 will be pumped on to neighbouring foam discs 20 on either side of the disc, and this pumped interlayer circulation results in further mixing of the liquid medium 6.

Figure 7A:
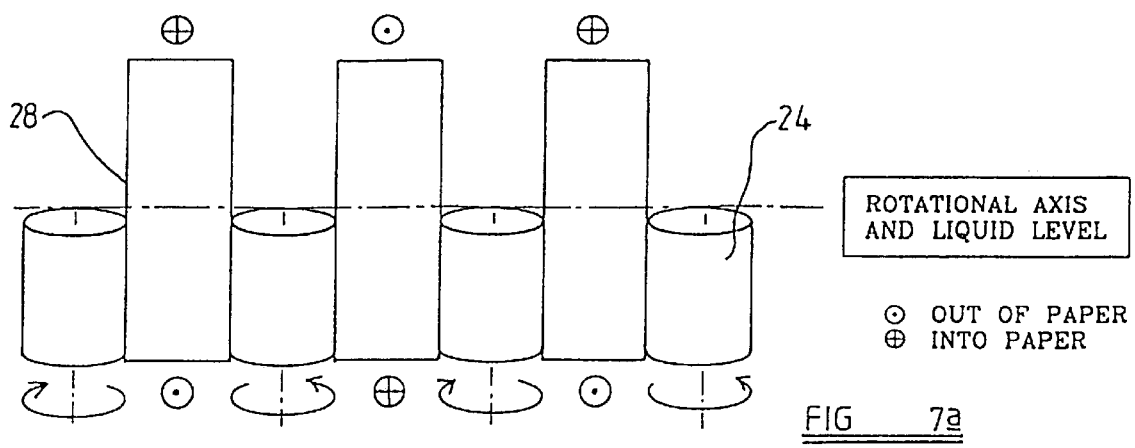
FIG. 7a shows a part-sectional, diagrammatical side view of part of an apparatus according to a fifth example of the present invention.
Figure 7B:
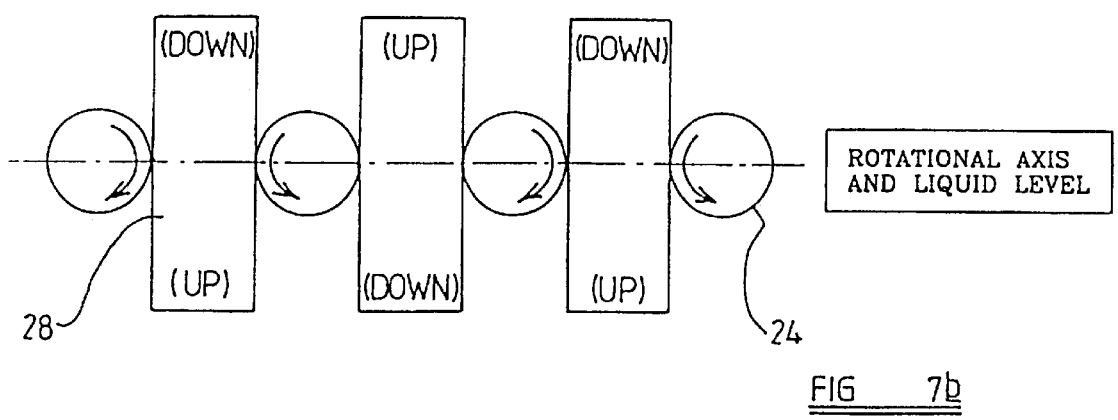

FIGS. 7a and 7b show a fifth example of the present invention. This example uses a plurality of foam discs 28, which are, again, arranged in the form of a rotating disc biocontactor. The foam discs 28 alternate with rollers 24, which are mounted vertically in the liquid medium 6 at the bottom of the trough 13, below the rotational axis, rather than horizontally along the liquid/gas interlayer in the plane of the rotational axis, as in the example of FIG. 5. The alternate foam discs 28 are rotated in opposite directions, as in the fourth example of the present invention and, as in the fourth example of the present invention, the compressive force is applied in a direction which is substantially perpendicular to the direction of travel of the foam.

It can be immediately realised that, in this example of the present invention, there is only one compressing and expanding step that is repeated in the liquid medium and there is no compressing and expanding step which aids gaseous intake, gaseous intake simply taking place as liquid drains from the foam in the gaseous phase. There is still, however, the effect of the pumped interlayer and intralayer local circulation previously described with reference to FIGS. 6a and 6b, which brings about an exchange of freshly mixed liquid between neighbouring foam discs 28 and between neighbouring parts of the same foam disc 28 and mass transfer of fluid is enhanced over prior art methods in which mass transfer of fluid is caused by simple diffusion, gravitational drainage or irrigational flow only. Also, the water level does not need to be fixed as in the example shown in FIG. 5.

Figure 8:
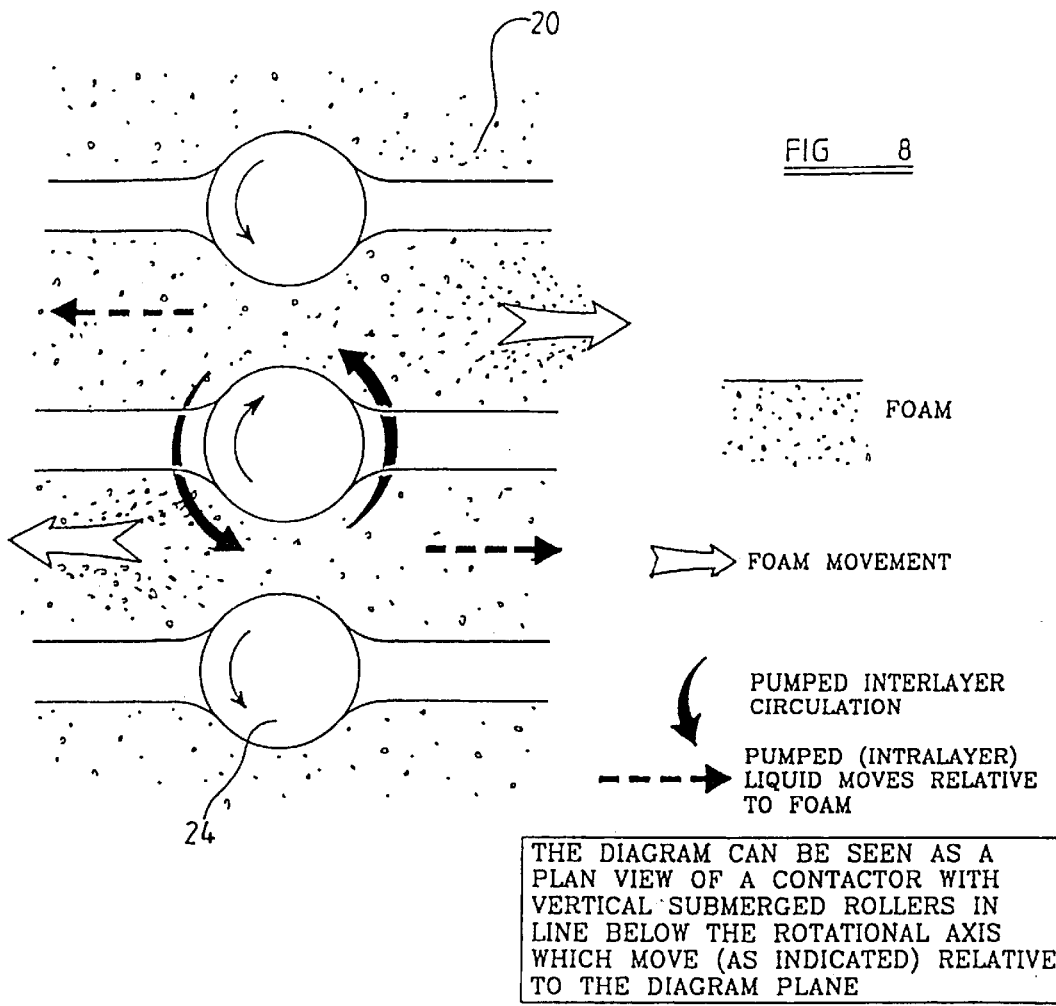
FIG. 8 is a diagrammatical illustration of flow patterns in the example of the apparatus shown in FIGS. 7a and 7b, viewed from above, and cross-sectional well below the rotational axis.

The pumped intralayer and interlayer local circulation, previously described, can be see more clearly in FIG. 8, which shows a top plan view of the foam discs 28 and rollers 24 of FIGS. 7a and 7b, cross-sectioned well below the rotational axis. FIG. 8 shows the direction of the pumped intralayer circulation (represented by the dotted arrow) caused by the compressive force exerted by the rollers 24 against the sides of the foam discs 20 (in a direction parallel to the rotational axis of the foam disc structures 22) and the direction of pumped interlayer circulation of liquid fluid (represented by the solid black arrows) caused by rotational movement of the rollers 24, between the foam discs 28.

A possible variation of the fifth example of the present invention, and which will not be described in detail, comprises a plurality of pieces of foam (not shown) which alternate with rollers (not shown), the rollers being mounted vertically in the liquid medium 6 at the bottom of a trough 13 in a manner similar to the example shown in FIGS. 7a, 7b and 8. Rather than being disc-shaped, however, as in the fifth example of the present invention, the foam pieces are in the form of rectangular slabs (not shown) which are moved backwards and forwards across the rollers in a linear direction. The foam slabs may all be moved in the same direction or, alternate slabs of foam may be moved in opposite directions. In this variation of the fifth example of the present invention, the liquid extrusion step is not mediated in co-operation with air intake but, again, the residual function of inducing relative motion between the foam matrix and its contained fluid, and exchange of fluid between neighbouring moving slabs of foam, remains and gives an increase of effectiveness over prior art methods in which flow is caused by simple diffusion, gravitational drainage or irrigational flow only. This variation also has the advantage that the foam slabs may be periodically withdrawn from the liquid medium for easy cell removal or cell harvesting.

Figure 9:
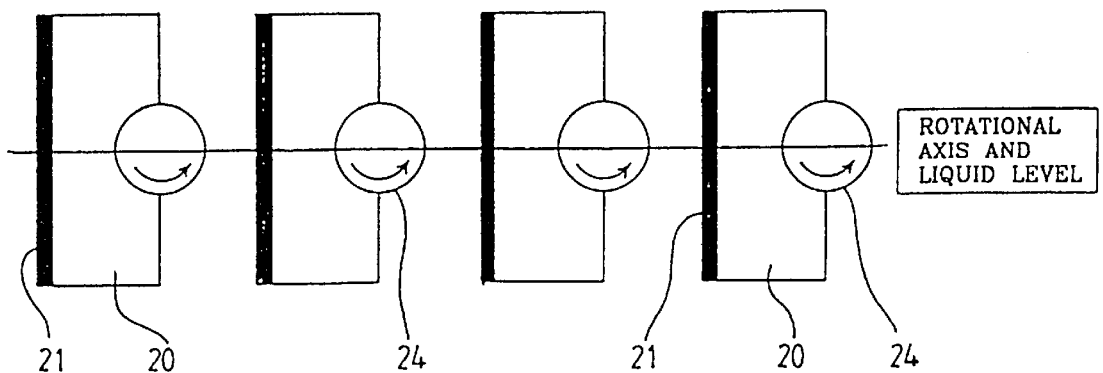
FIG. 9 shows a diagrammatical side view of part of an apparatus according to a sixth example of the present invention.

FIG. 9 shows a sixth example of the present invention, which is similar to the fourth example of the present invention shown in FIG. 5, except that, instead of providing a pair of circular foam discs 20 on either side of a central, perforated, circular rigid disc 21, a single circular foam disc 20a is provided on one side only of a rigid, waterproof, circular disc 21a.

In the same way as in FIG. 5, the resulting composite disc structures 22a are mounted for rotation about a central axis shaft 23 and the central axis shaft 23 is preferably hollow and perforated to act as a liquid inlet. Along the axis of rotation, the composite discs structures 22a alternate with rollers 24, although, contrary to the example shown in FIGS. 5 and 6, each roller 24 presses against the adjacent disc structure 22a on one side thereof and a gap is provided between each roller 24 and the next adjacent rigid, waterproof, disc 21a on the other side thereof. The disc structures 22a may, therefore, all be rotated in the same direction which allows a single drive mechanism (not shown) to be provided at one end of the rotational axis. The rollers 24 are passive followers of the driven disc structures 22a.

In the same way as in the fifth example of the present invention, the rollers 24 are arranged to apply a compressive force against the disc structure 22a, in a direction which is substantially perpendicular to the direction of travel of the foam, thereby squeezing the area of foam in contact with the rollers 24 between the rollers 24 and the rigid discs 21a as the disc structures 22a rotate. The extent of the compressive force applied may be varied, simply by varying the distance between the rollers 24 and the rigid, waterproof, discs 21a. This example of the present invention is particularly useful for discharging calls from the foam, which can be easily achieved by providing, for example, a linked mounting movable as a whole relative to the disc structures 22a to reduce the spacing between the rollers 24 and the rigid, waterproof, discs 21a with a quick, smooth, single action.

Whilst this example of the present invention is not so compact as the fifth example of the present invention, it has a simpler construction.

Figure 10A:
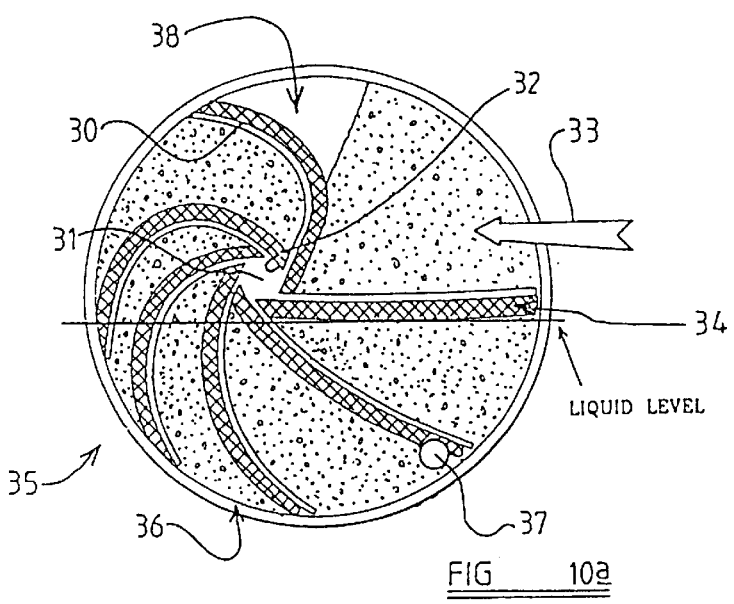
FIG. 10a shows a diagrammatical front view of part of an apparatus according to a seventh example of the present invention, with the foam structure in a first arrangement (the foam sectors have been omitted for clarity)

FIGS. 10a to 10e show a seventh example of the present invention. The structure of this example of the present invention comprises six elongate strips 30 of a flexible, elastic, waterproof material, preferably fibre-reinforced, mounted on a central hexagonal member 31, one strip 30 extending from each flat side 32 of the hexagonal member 31. (Any other suitable polygonal member may, of course, be used, with a corresponding number of elongate strips). The elongate strips 30 form six sector walls and between the sector walls 30, are provided six foam sectors 33 of equal size, formed from a suitable, at least partially open-celled foam such as, for example, a compressible and resilient, reticulated polyurethane foam. The radial edge of the leading side of each foam sector 33 is firmly secured to the adjacent sector wall 30, whereas the radial edge of the trailing side of each foam sector 33 remains unattached. A layer of coarse material or drainage mat 34, which acts as a flow channel, is attached to the leading side of each sector wall 30, as shown in FIG. 10a. The coarse material 34 may comprise, for example, an open woven filamentous material such as a melt-blown plastic mesh, an open polyvinyl chloride matting or semi-rigid corrugated polyvinyl chloride sheet or a much more coarse and incompressible foam than that of the foam sectors 33. The coarse material 34 may, alternatively, be attached to the trailing sides of the foam sectors 33 rather than to the leading sides of the sector walls 30.

The resulting foam structure is located, in use, within a rotating cylindrical drum 35 and may be linked in the axial direction to a plurality of other foam structures that, together, rotate as a single composite structure (not shown). The length of each sector wall 30 exceeds the internal radius of the drum 35 and the foam structure is mounted inside the drum 35 with the hexagonal member 31 eccentrically positioned with respect to the central rotational axis of the drum 35, to the extent that, on one side of the drum 35, (the right hand side in FIG. 10), there is a region where one or more sector walls 30 do not reach (or only just reach) the cylindrical drum wall 36 and, on the opposing side of the drum 35, (the left hand side in FIG. 10), one or more sector walls 30 abut and curve against the cylindrical drum wall 36, in the direction of rotation, in use. The hexagonal member 31 is mounted for rotation on a shaft (not shown) within the drum 35 and, because of the positioning of the hexagonal member 31 within the drum 35, the foam structure will rotate about an axis which is parallel to, and spaced apart from, the central rotational axis of the drum 35. Vertical movement of the hexagonal member 31 on the shaft is prohibited.

One part of the cylindrical wall 36 of the drum 35 forms the bottom of the drum 35 and the bottom of the drum 35 is filled with a liquid medium up to a level just below the hexagonal member 31, such that the foam structure is partially submerged. Below the liquid level, and adjacent the cylindrical drum wall 36, at a position where the end of a sector wall 30 is about to make contact and curve against the cylindrical drum wall 36 (on the right hand side of the drum in FIG. 10), there is further provided an obstructing member 37 which is static and temporarily hinders forward movement of an approaching sector wall 30 as the foam structure rotates.

Figures 10B, 10C:
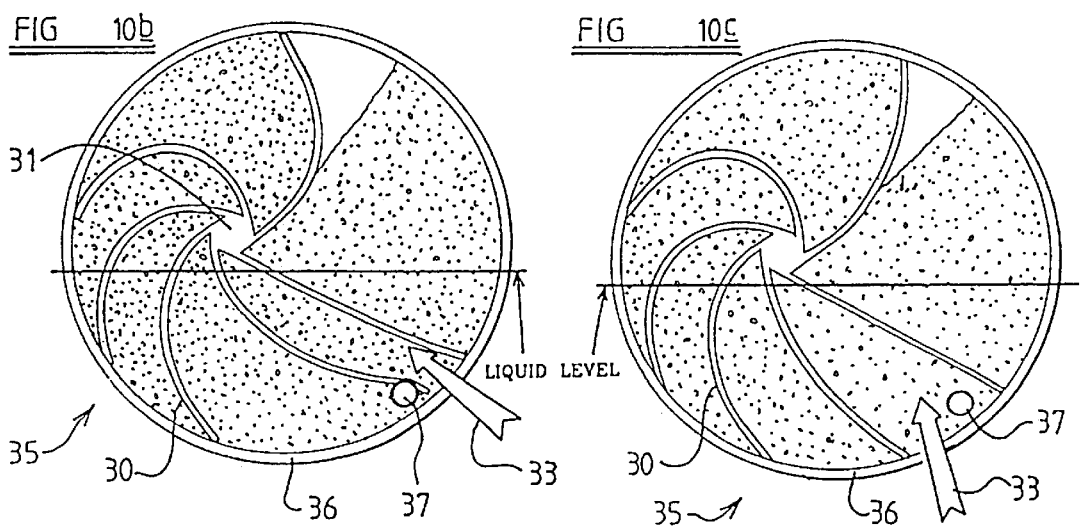
FIG. 10b shows a diagrammatical front view of the apparatus of FIG. 10a, with the foam structure in a second arrangement (the foam sectors have been omitted for clarity)
FIG. 10c shows a diagrammatical front view of the apparatus of FIG. 10a, with the foam structure in a third arrangement (the foam sectors have been omitted for clarity)
Figures 10D, 10E:
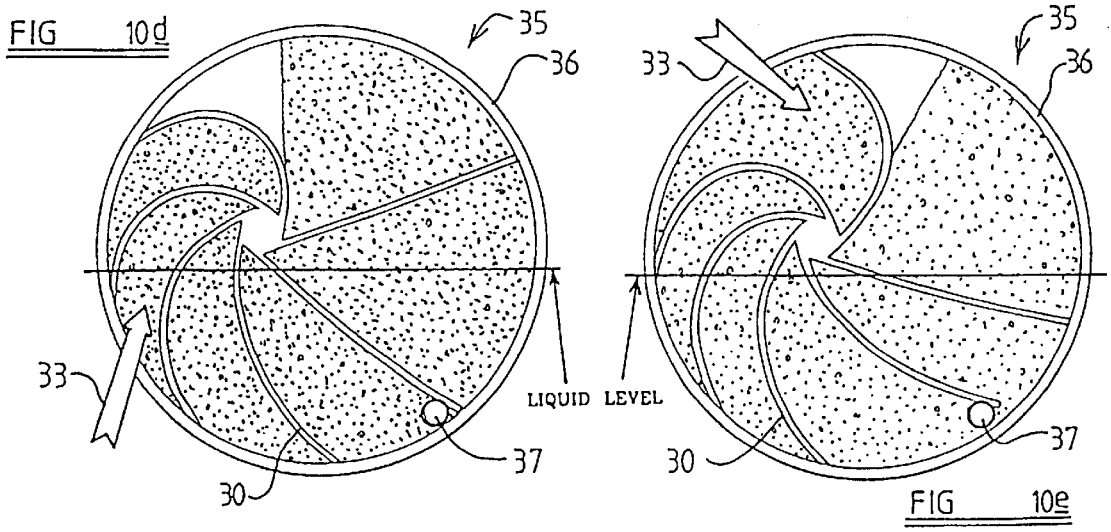
FIG. 10d shows a diagrammatical front view of the apparatus of FIG. 10a, with the foam structure in a fourth arrangement (the foam sectors have been omitted for clarity)
FIG. 10e shows a diagrammatical front view of the apparatus of FIG. 10a, with the foam structure in a fifth arrangement (the foam sectors have been omitted for clarity)

Both the drum 35 and the foam structure are rotated at the same rate at, for example, approximately 0.5 revolutions per minute and in the same direction (clockwise in FIG. 10). The foam structure is rotate so that a foam sector 33 moves past the narrowest gap between the hexagonal member 31 and the drum wall 36 as the foam sector 33 is transferred from the liquid medium to the gaseous medium (on the left hand side of the drum in FIG. 10), and past the obstructing member 37 following entry of the foam sector 33 from the gaseous medium into the liquid medium (on the right hand side of the drum in FIG. 10). As in the third to sixth examples of the present invention, as the foam structure rotates, a major part of each foam sector 33 is submerged and is then lifted out of the liquid medium again, so that the foam sectors 33 are alternately exposed to liquid and gaseous media. FIGS. 10a to 10e illustrate the sequence of steps involved when the drum 35 and foam structure are rotated in this way.

Following the progression of a single foam sector 33 (marked with an arrow) through the cycle of FIGS. 10a to 10e, it can be realised from FIG. 10a that a foam sector 33 is in its fully expanded state in the gaseous medium just before immersion into the liquid medium. As this foam sector 33 rotates into the liquid medium, movement of the sector wall 30 on the leading side of the foam sector 33, and to which the foam sector 33 is attached, is temporarily arrested against the obstructing member 37 in the drum 35, such that the sector wall 30 on the trailing side of this foam sector 33, which is still in motion, compresses the foam sector 33 between adjacent sector walls 30. This step corresponds functionally with step 3 of FIGS. 1 and 2, i.e. the de-gassing step, and here, the compressive force is applied substantially in the direction of travel of the foam sector 33. FIG. 10b shows the foam sector 33 (marked with an arrow) at maximum squeeze.

The foam sector 33 will continue to rotate around the drum 35 until the sector wall 30 on the leading side of the foam sector 33 flips past the obstructing member 37, at which point, the compressed foam sector 33 will begin to expand again due to its natural resiliency (decompressibility) as can be seen in FIG. 10c. This corresponds functionally with step 4 in FIGS. 1 and 2 of the accompanying drawings.

As the foam sector 33 continues to rotate around the drum 35 and reaches the other side of the drum 35, the asymmetrical positioning of the hexagonal member 31 means that the sector wall 30 on the leading side of the foam sector 33 now begins to curve against the cylindrical drum wall 36, with an increasing amount of tension as the angle between the leading and trailing sides of the foam sector 33 decreases. This, again, serves to compress the foam sector 33 between adjacent sector walls 30, with maximum squeeze occurring as the foam sector 33 begins to emerge from the liquid medium into the gaseous medium (see FIG. 10d). This step corresponds functionally with step 7 of FIGS. 1 and 2, i.e. the water extrusion step, and, here, the compressive force comprises components applied both in the direction of travel of the foam sector 33 and in a direction which is substantially perpendicular thereto.

The tension in the sector wall 30 on the leading side of the foam sector 33 is then gradually released as the foam sector 33 rotates further around the drum 35 and the angle between the leading and trailing sides of the foam sector 33 increases, such that the foam sector 33 begins to expand again, corresponding functionally with step 8 in FIGS. 1 and 2 (see FIG. 10e). Maximum expansion occurs just as the foam sector 33 is about to be immersed in the liquid medium again as shown in FIG. 10a. This sequence of events then repeats.

As the foam sector 33 expands in the gaseous medium, a gap 38 forms between the sector wall 30 and the edge of the foam sector 33 on the trailing side of the foam sector 33. This gap 38 can be clearly seen in FIG. 10a. As the foam sector 33 rotates towards the liquid medium again, the curved edge of the sector wall 30 on the trailing side of the foam sector 33 will straighten out as the angle between the leading and trailing sides of the foam sector 33 increases, and the sector wall 30 on the trailing side of the foam sector 33 will, at this point, tend to flip over against the trailing edge of the foam sector 33, thereby closing the gap 38 between the sector wall 30 and foam sector 33. This contributes to onward motion of the foam sector 33 and aids foam tumbling.

FIG. 11 shows an eighth example of the present invention, which is similar to the seventh example of the present invention, except that the foam sectors 33 are separated by strips of a softer, more flexible, waterproof material and there is no obstructing member 37. The only compressing and expanding step is, thus, that caused by the asymmetrical positioning of the hexagonal member 31, whereby the foam sectors 33 are compressed as they rotate past the narrowest gap between the hexagonal member 31 and the drum wall 36 (on the left hand side of the drum 35 in FIG. 11) and expand again as they progress towards the widest gap between the hexagonal member 31 and the drum wall 36 (on the right hand side of the drum 35 in FIG. 11). Thus, in this example of the present invention, only a single compressing and expanding step is repeated which corresponds functionally with the water extrusion step 7 of FIGS. 1 and 2, and there is no second compressing and expanding step which corresponds to the de-gassing step 3 of FIGS. 1 and 2. Mass transfer of gaseous and liquid fluid into and out of the foam is still, however, enhanced over prior art methods of simple diffusion, gravitational drainage and/or irrigational flow only.

FIGS. 12a and 12b show a ninth example of the present invention, which is a variation of the construction shown in FIGS. 10a to 10e.

Instead of the static obstructing member 37 of FIGS. 10a to 10e, this example of the present invention uses a buoyant obstructing member or float 39 which, in the context of FIGS. 10a to 10e, exerts an upward floatational force on a descending foam sector 33 thereby acting to de-gas it. The float 39 is free to move in a restricted region and may be moored, although it does not necessarily need to be fixed.

As a foam sector 33 passes over the float 39, the foam sector 33 distorts and is dragged over the slightly sloping upper surface of the float 39. Once a foam sector 33 has passed over the float 39, the buoyancy of the float 39, expansion of the foam sector 33 that has just passed over the float 39, and geometric changes all combine to ease the float 39 back into its original starting position, and prevent the float 39 from being carried around by the moving foam.

In order to provide sufficient upward force to de-gas the foam in this example of the present invention, the float 39, preferably, occupies approximately 6% of rotor volume.

The float 39 of FIG. 12a is shown in more detail in FIG. 12b and comprises a shaped piece of rigid closed-cell foam which is highly buoyant. The float 39 has an undulating top surface 40 and channels 41 formed vertically therethrough, all of which serves to aid fluid movement. One of the side surfaces of the float 39 is curved to correspond to the side wall 36 of the cylindrical rotating drum 35. This curved surface 42 of the float 39 is, preferably, arranged to slope on the wall 36 of the rotating drum 35, for example, on nylon runners (not shown).

Figure 13:
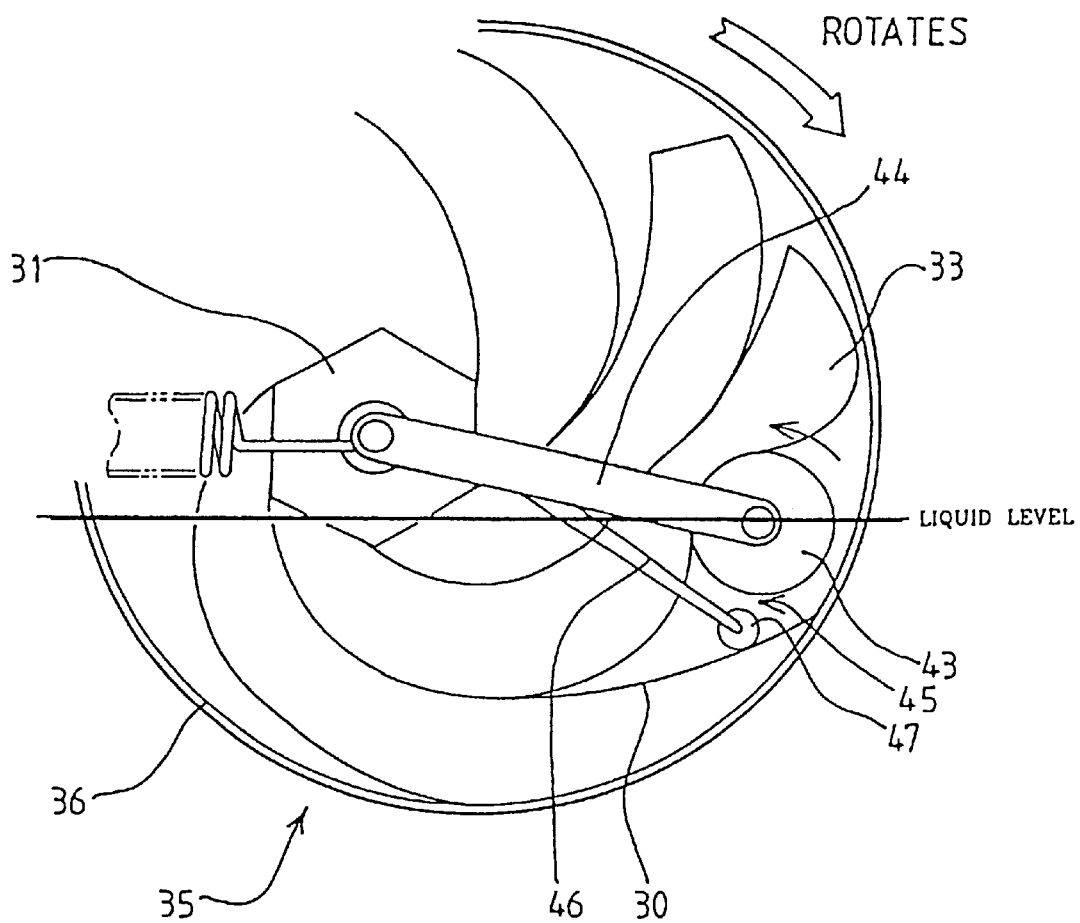
FIG. 13 shows a diagrammatical front view of part of an apparatus according to a tenth example of the present invention.

FIG. 13 shows a tenth example of the present invention, which is a further variation of the constructions shown in FIGS. 10a to 10e and FIGS. 12a and 12b.

Instead of the static obstruction member 37 of FIGS. 10a to 10e, this example of the present invention uses a buoyant obstructing member or float 43, similar to the float 39 of FIGS. 12a and 12b, except that the float 43 of FIG. 13 is cylindrical, and is held parallel to and at a fixed distance from the rotating hexagonal member 31 by means of an arm 44. In addition, the hexagonal member 31 of this example of the present invention is, itself, tensioned, by any suitable means, towards the wall 36 of the drum 35 nearest to it (i.e. towards the left-hand wall of the drum 35 in FIG. 13).

The fixed distance between the hexagonal member 31 and the cylindrical float 43 enhances squeezing of a descending foam sector 33, as does movement of the cylindrical float 43 across the leading face of the descending foam sector 33, and the fact that the upward pressure of the float 43 is exerted over a smaller area than in the example shown in FIGS. 12a and 12b. As a consequence, the volume of the cylindrical float 43 of this example of the present invention can be less than the volume of the float 39 in the ninth example of the present invention.

The example of the present invention shown in FIG. 13 also requires a gap 45 between the cylindrical float 43 and the trailing side of the foam sector 33 beneath it (see FIG. 13). This gap 45 is required to avoid float/foam friction and may either form spontaneously or may, for example, be provided by means of a mini-roller 46 attached to the arm 44 connecting the hexagonal member 31 and the cylindrical float 43. The mini-roller 46 in FIG. 13 is angled downwardly from the arm 44, with the roller head 47 of the mini-roller 46 in contact with the radial edge of the trailing side of the foam sector 33 beneath it.

The obstructing members 37, 39 and 43 of examples 7, 9, and 10 of the present invention may, of course, also be used with the construction of the eighth example of the present invention shown in FIG. 11.

As can be seen, examples seven to ten of the present invention have a very simple construction, which dispenses with the rotor drive mechanism and escapement catches of the example shown in FIG. 3 of the accompanying drawings, and the rollers 24 of the examples shown in FIGS. 5 to 8 of the accompanying drawings. Examples seven to ten of the present invention also have lower energy requirements and it will be appreciated that the construction of these examples of the present invention may be modified to particular design requirements simply by altering, for example, the position of the hexagonal member 31 (and the obstructing members 37, 39 in examples seven, none and ten) in the rotating cylindrical drum 35.

It should be noted that in all of the above described examples of the present invention, the devices used to not depend on the exact dimensions of the foam pieces so that a certain amount of wear and tear of the foam will not affect the efficiency of the systems used.

A person skilled in the art will appreciate that, in any system containing growing cells, the cells will multiply and excess cells may need to be removed from the system in order to make room for further multiplication. This may be done by conventional methods, for example, by stronger squeezing or rolling of the foam, or by applying a squirting action. In this case, the excess cells will be discharged to the liquid medium 6 and subsequently, to effluent. It may be necessary, in certain cases to remove the cells from the effluent and this may, again, be carried out by conventional means, for example, by way of a bed of foam which can be used to filter out cells which are then extruded as a paste by squeezing or rolling the foam bed. Any filtrate obtained may then be returned to the reactor, depending on the particular application or use concerned.

As stated previously, inoculation of the foam with suitable microorganisms, plant or animal cells may also be carried out by conventional means. Simply moving the foam through a culture is likely to result in the trapping of cells in the matrix of the foam, although care will, of course, need to be taken to ensure evenness of inoculation, again, as explained previously. The foam provides a substantial voidage which gives a protective environment to support the growth of biomass, and the biomass will tend to propagate and migrate through the interconnected spaces of the foam to colonise the foam body. Provisions may also be made to remove the foam from the equipment for replacement or cleaning.

Where cells are to be harvested, for example, in a desalination process, or in the production of chemical or pharmaceutical products, the simplest type of system according to the present invention which would be adaptable to the needs of such a process would be those such as shown in FIGS. 5 to 9, in which the roller separation could be much reduced so that a paste of harvested cells may be extruded. Alternatively, foam pieces could be removed to a separate device for harvesting of cells.

The specifications of the apparatus of the present invention may be adapted to suit particular applications or uses. For example, it will be usual to provide the bioreactors in relevant cases with an influent fluid stream and effluent weir to provide a continuous system. The components of the gaseous 5 and liquid 6 media may be varied and steps may, for example, be taken to replenish the gaseous medium 5 with a particular gas such as oxygen, or to remove a particular gas produced by the system, such as ammonia. Provision may also be made to increase the mass transfer of gaseous fluid still further, for example, by flowing a particular gas, such as air or oxygen, through the foam during the gaseous phase. In this case, however, care would need to be taken to avoid differential drying of the foam and further energy consumption would be required.

In the case of the production of chemical and pharmaceutical products, adaptions will need to be made to ensure that the process meets sterile and other regulatory requirements.

Where the present invention is to be used for the treatment of organic residues such as animal slurries, it will be likely that the slurry will need to be pre-treated before being introduced into the apparatus of the present invention. For example, it will be clear to a person skilled in the art that a straining element would need to be introduced into the apparatus of the present invention for preliminary straining of, for example, pig slurry. Other adaptions would then need to be made for collecting the desired end product and separating out waste products, depending on the particular application or use concerned.

In the treatment of waste water and/or organic residues such as animal slurries, the product obtained by the methods of the present invention may be passed sequentially through a series of apparatus according to the present invention, or transferred, for example, for purification by a further cleaning process. The product may, alternatively, be discharged to sewer (at reduced costs compared to the untreated product) or discharged to the environment, with or without further treatment, depending on the particular regulations that apply.

In the case of the potential use of the methods and apparatus of the present invention in a desalination process, there should ideally be a net uptake of alkali cations from the treated product, and viable microorganisms which are capable of growing in an appreciably saline environment, such as halobacteria, would be required. Cells in the system may be harvested by intense rolling of the foam whilst washing the foam with a non-aqueous solution of such composition that the cells would retain their salt. The cell suspension so obtained could then be filtered to obtain a salty cake, and the non-aqueous filtrate returned to be re-used in the wash cycle.

With regard to the use of the method and apparatus of the present invention in the petroleum industry, the porous matrix system may be loaded with suitable microorganisms and used, for example, in processes for mineralisation of organic carbon atoms and degradation of organic materials, including oil or fuel hydrocarbons. The apparatus and method of the present invention, thus, have potential uses in processes for refining oil or petroleum, for removing or degrading contaminants in oil or petroleum, and for cleaning up environmental contaminations resulting from fuel leaks. In the latter context, the method and apparatus of the present invention would be suitable for use in, for example, tankers, tanker bilge, waste water, ballast water or washing water release, submarine oil fields, petrochemical complexes, the release of oil-containing waste water from oil refineries or petrochemical plants, and in ex situ or in situ bioremediation. The apparatus and method of the present invention may also find uses in the processing or degradation of oil and petroleum-derived products and/or contaminants thereof.

In a further application of the invention in the petroleum industry, it is envisaged that the substrate for the metabolising biomass may be a fuel by-product or a fossil fuel, and that residues of the metabolic process may be dried and used as a fuel source, for example in the form of nuggets or a pulverised dust.

Thus, it is readily apparent that the methods and apparatus of the present invention are easily adaptable for many different uses.

What is claimed is:

1. Apparatus for enhancing a biological process, said apparatus comprising a reaction vessel for containing a fluid medium of first and second fluid media, a porous matrix system comprises a cylindrical disc of foam divided into a plurality of foam sectors by means of a plurality of impervious septa, compressing means comprising an escapement catch for arresting movement of a first septum, drive means for driving a second septum toward the first septum to compress the foam therebetween, means for applying a series of controlled compressive forces to a region of said porous matrix system, each compressive force applied to a foam sector being releasable and effective to extrude fluid but not significant biomass contained in the porous matrix system, means for controllably expanding the region of the porous matrix system in the fluid medium following release of a compressive force, and means for transferring the region of porous matrix system from one fluid medium to the other between repeated expanding steps with the compressive force being applied substantially in the direction of travel of the region of foam.

2. Apparatus according to claim 1, wherein the reaction vessel comprises a first section containing the first fluid medium, in use, and a second section containing the second fluid medium, in use, the diameter of the porous matrix system spanning both the first and second sections, and wherein the means for transferring the region of the porous matrix system from one fluid medium to the other comprises means for rotating the foam disc in the reaction vessel.

3. Apparatus according to claim 2, wherein the means for rotating the foam disc comprises the compressing means.

4. Apparatus according to claim 1, wherein the porous matrix system comprises a plurality of foam discs aligned in the axial direction.

5. Apparatus according to claim 1, wherein each foam sector is provided with a plurality of radially arranged flow channels, and a plurality of concentrically arranged drainage lamina which are graded in their flow capacity in the direction of fluid flow.

6. Apparatus for enhancing a biological process, said apparatus comprising a reaction vessel for containing first and second fluid media, a plurality of disc structures mounted for rotation about a common rotational axis, each disc structure comprising a pair of foam discs on either side of a central, rigid, disc and means for applying a series of controlled compressive forces to a region of said porous matrix system, said means comprises a plurality of rollers which alternate with the disc units, the spacing between the rollers and disc units being such that the rollers apply a compressive force against the foam to compress the foam between the rollers and rigid disc, each compressive force being releasable and effective to extrude fluid, but not significant biomass, contained in the porous matrix system, means for controllably expanding the region of the porous matrix system in the fluid medium following release of a compressive force, and means for transferring the region of the porous matrix system from one fluid medium to the other between repeated expanding steps.

7. Apparatus according to claim 6, wherein the reaction vessel comprises a circular trough and wherein the rollers are arranged vertically in the bottom of the trough below the rotational axis of the disc units.

8. Apparatus according to claim 6, wherein the reaction vessel is divided into a first section containing a first fluid medium, in use, and a second section containing a second fluid medium, in use, the diameter of each disc unit spanning the first and second sections, and wherein the means for transferring the region of the porous matrix system from one fluid medium to the other comprises means for rotating the disc units in the reaction vessel.

9. Apparatus according to claim 8, wherein alternate discs are rotated in opposite directions and wherein each roller comprises a plurality of bobbins of equal radii rotatable about a roller spindle which lies substantially in the plane of the rotational axis of the disc units, with the rotational axis of the bobbins perpendicular to the rotational axis of the disc units, and wherein the rollers are provided at the interface between the first and second sections, in use.

10. Apparatus for enhancing a biological process, said apparatus comprising a reaction vessel for containing a fluid medium of first and second fluid media, a porous matrix system comprising a central polygonal member, a plurality of elongate flexible members, one flexible member mounted on each face of the polygonal member, a plurality of foam sectors arranged between the flexible members, with a leading face of each foam sector attached to an adjacent flexible member, means for applying a series of controlled compressive forces to a region of said porous matrix system, said means arresting movement of a first flexible member and means for driving a second flexible member towards the first flexible member to compress a foam sector therebetween, each compressive force applied to a foam sector being releasable and effective to extrude fluid, but not significant biomass, contained in the porous matrix system, means for controllably expanding the region of the porous matrix system in the fluid medium following release of a compressive force, and means for transferring the region of the porous matrix system from one fluid medium to the other between repeated expanding steps with the compressive force being applied substantially in the direction of travel or perpendicular to direction of travel of the foam sectors.

11. Apparatus according to claim 10, wherein the reaction vessel comprises a drum which rotates, in use, the drum having a radius which is smaller than the radii of the flexible members, and wherein the polygonal member is mounted for rotation within the drum at a position which is eccentric to the central rotational axis of the drum.

12. Apparatus according to claim 11, wherein the polygonal member is tensioned towards a wall of the drum.

13. Apparatus according to claim 11, wherein a first arresting means is provided on one side of the drum and comprises a wall of the drum, and a second arresting means is provided on another side of the drum and comprises an obstructing member positioned in the path of a moving flexible member.

14. Apparatus according to claim 13, wherein the obstructing member is static.

15. Apparatus according to claim 13, wherein the obstructing member is buoyant.

16. Apparatus according to claim 15, wherein the obstructing member comprises a float which is held parallel to and at a fixed distance from the polygonal member.

17. Apparatus according to claim 10, wherein the reaction vessel is divided into a first section containing a first fluid medium and a second section containing a second fluid medium the diameter of the porous matrix system spanning the first and sections, and wherein the means for transferring the region of the porous matrix system from one fluid medium to the other comprises a rotor for rotating the polygonal member.

18. Apparatus according to claim 17, wherein the porous matrix system comprises an at least partially open-celled foam of a compressible and resilient plastics material.

19. Apparatus according to claim 18, wherein the foam comprises a compressible and resilient, plastics material, reticulated foam.

20. Apparatus according to claim 18, wherein the expansion means comprises a natural resiliency or decompressibility of the foam.

21. Apparatus according to claim 10, wherein the expansion means comprises a resilient band or strip which acts to pull a compressed region of the porous matrix system back into its natural resting position.

22. A method for enchanting mass transfer of a fluid in a porous matrix system, which method comprises the steps of (a) rotating a foam disc in a reactor vessel, the reactor vessel comprising a first section containing a first fluid medium, in use, and a second section containing a second fluid medium, in use, the diameter of the foam disc spanning the first and second sections, (b) applying a compressive force to the foam disc along the interface between the first and second sections, the compressive force being controllably applied to a region of the porous matrix system, being applied in a direction which is substantially perpendicular to the direction of travel of the region of foam and being effective to extrude fluid but not significant biomass contained in the porous matrix system, (c) releasing the compressive force, (d) controllably expanding the region of the porous matrix system in a medium containing said fluid, (e) transferring the region of the porous matrix system from one to another of first and second fluid media before repeating step (d), and repeating steps (a) to (e).

23. A method according to claim 22, further comprising the step of applying a rotational force along the interface between the first and second fluid media, in a clockwise direction on one side of the foam disc and in an anti-clockwise direction on the other side of the foam disc to aid fluid circulation and mixing.

24. A method for enchanting mass transfer of a fluid in a porous matrix system, said method comprising the steps of (a) immersing a piece of foam in a liquid medium, (b) applying a compressive force along a substantially vertical axis of the piece of foam (c) moving the piece of foam across the substantially vertical axis in either a linear or rotational direction, the compressive force being applied in a direction which is substantially perpendicular to the direction of travel of the region of foam and being effective to extrude fluid but not significant biomass contained in the porous matrix system, (d) releasing the compressive force, (e) controllably expanding the region of the porous matrix system in a medium containing said fluid, (f) transferring the region of the porous matrix system from one to another of first and second fluid media before repeating step (e), and repeating steps (a) to (f).

25. A method according to claim 24, comprising the further step of applying a rotational force about the vertical axis to aid fluid circulation and mixing.

26. Apparatus for enhancing a biological process in which a biomass is contacted with a gas and with a nutrient liquid, the apparatus including a resiliently compressible porous matrix system for containing said biomass, a reaction vessel containing a body of said liquid and a body of said gas above the body of liquid, the body of liquid having an upper surface exposed to said body of gas and defining a liquid-gas interface, mounting means mounting said porous matrix system in the reaction vessel at a position in which said compressible porous matrix system is partly immersed in said liquid medium in the reaction vessel and partly extends above said upper surface of the liquid into said body of gas, said mounting means mounting said porous matrix system for rotation about an axis with a substantial horizontal component, means for rotating said porous matrix system about said axis and means for periodically compressing and expanding regions of said porous matrix system.

27. Apparatus according to claim 26, wherein said resiliently compressible porous matrix system comprises a plurality of disc structures mounted for rotation about a common rotational axis, each disc structure comprising a pair of foam discs on either side of a central, rigid, disc and wherein the compressing means comprises a plurality of rollers which alternate with the disc units, the spacing between the rollers and disc units being such that the rollers apply a compressive force against the foam to compress the foam between the rollers and rigid discs.

28. Apparatus according to claim 26, wherein said resiliently compressible porous matrix system comprise a central polygonal member, a plurality of elongate flexible members, one member mounted on each face of the polygonal member, and a plurality of foam sectors arranged between the flexible members, with a leading face of each foam sector attached to an adjacent flexible member, and wherein said means for periodically compressing means comprises means for arresting movement of a first flexible member and means for driving a second flexible member towards the first flexible member to compress a foam sector therebetween.

29. Apparatus according to claim 28, wherein said reaction vessel comprises a rotatable drum having a radius which is smaller than the radii of the flexible members, and wherein said central polygonal member is mounted for rotation within said drum at a position which is eccentric to the central rotational axis of the drum.

30. Apparatus according to claim 29, wherein the mounting of said central polygonal member tensions the polygonal member towards a wall of said drum.

31. The apparatus according to claim 29, wherein a first arresting means is provided on one side of the drum and comprises a wall of the drum, and a second arresting means is provided on another side of the drum and comprises an obstructing member positioned in the path of a moving flexible member.

32. Apparatus according to claim 31, wherein the obstructing member is static.

33. Apparatus according to claim 31, wherein the obstructing member is buoyant.

34. Apparatus according to claim 33, wherein the obstructing member comprises a float which is held parallel to and at a fixed distance from the polygonal member.

35. Apparatus according to claim 28, wherein the reaction vessel is divided into a first section containing said nutrient liquid and a second section containing said gas, the diameter of the porous matrix system spanning the first and second sections, and wherein said means for rotating said porous matrix system, comprises a rotor for rotating the polygonal member.

36. Apparatus according to claim 26, wherein said porous matrix system comprises an at least partially open-celled foam.

37. A method for enhancing a biological process in which a biomass is contacted with a gas and with a nutrient liquid, the method including providing apparatus including; a reaction vessel, a resiliently compressible porous matrix system, mounting means mounting said porous matrix system in the reaction vessel for rotation about an axis with a substantial horizontal component, means for rotating said porous matrix system about said axis and means for periodically compressing and expanding regions of said porous matrix system, the method comprising providing in said reaction vessel a body of said liquid and a body of said gas above the body of liquid, whereby the body of liquid has an upper surface exposed to said body of gas and defining a liquid-gas interface, locating said biomass in said resiliently compressible porous matrix system, rotating said resiliently compressible porous matrix system about said axis and, periodically compressing and expanding regions of said porous matrix system to effect mass transfer of said liquid medium and said gaseous medium in the porous matrix system.

38. A method according to claim 37, wherein the compressive force is applied in a direction which is substantially perpendicular to the direction of travel of the region of porous matrix.

39. A method according to claim 37, which method comprises the steps of selecting a foam disc to form part of said porous matrix for rotation in said reactor vessel, the reactor vessel comprising a first section containing said fluid and a second section containing said gas, the diameter of the foam disc spanning the first and second sections, and said step of periodically compressing and expanding includes applying a compressive forced to the foam disc along the interface between the first and second sections.

40. A method according to claim 39, further comprising the step of applying a rotational force along the interface between the first and second fluid media, in the clockwise direction on one side of the foam disc and in an anti-clockwise direction on the other side of the foam disc to aid fluid circulation and mixing.

41. A method according to claim 37, comprising the step of immersing a piece of foam in a liquid medium, applying a compressive force along a substantially vertical axis of the piece of foam and moving the piece of foam across the substantially vertical axis in either a linear or rotational direction.

42. A method according to claim 41, comprising the further step of applying a rotational force about the vertical axis to aid fluid circulation and mixing.

\* \* \* \* \*